United States Patent [19]

Henrick et al.

[11] 4,411,912

[45] Oct. 25, 1983

[54] INSECTICIDAL ISOVALERIC ACID ESTERS

[75] Inventors: Clive A. Henrick, Palo Alto; Barbara A. Garcia, Boulder Creek, both of Calif.

[73] Assignee: Zoecon Corporation, Palo Alto, Calif.

[21] Appl. No.: 93,553

[22] Filed: Nov. 13, 1979

Related U.S. Application Data

[60] Division of Ser. No. 878,091, Feb. 16, 1978, Pat. No. 4,243,819, which is a continuation-in-part of Ser. No. 824,947, Aug. 15, 1977, abandoned, which is a continuation-in-part of Ser. No. 779,886, Mar. 21, 1977, abandoned.

[51] Int. Cl.$^3$ .................... A01N 37/34; A01N 37/44; C07C 101/44; C07C 121/78

[52] U.S. Cl. ................................. 424/304; 260/455 R; 260/465 D; 424/274; 424/275; 424/282; 424/285; 424/301; 424/309; 548/477; 548/513; 549/76; 549/496; 549/439; 560/9; 560/22; 560/43

[58] Field of Search ........... 260/326.43, 347.4, 455 R, 260/465 D; 549/76, 439, 496; 560/43, 125, 9, 22; 424/304, 305, 309, 274, 275, 282, 285, 301; 548/477, 513

[56] References Cited

U.S. PATENT DOCUMENTS 4,161,537  7/1979  Katsuda et al. ..................... 424/304
4,201,787  5/1980  Katsuda et al. ..................... 424/304

Primary Examiner—Dolph H. Torrence
Attorney, Agent, or Firm—Donald W. Erickson; Douglas G. Brace; Paul H. Heller

[57] ABSTRACT

Esters and thiolesters of amino acids, intermediates therefor, synthesis thereof, and the use of said esters and thiolesters and compositions for the control of pests.

63 Claims, No Drawings

INSECTICIDAL ISOVALERIC ACID ESTERS

This is a division of application Ser. No. 878,091, filed Feb. 16, 1978, U.S. Pat. No. 4,243,819, which is a continuation-in-part of Ser. No. 824,947, filed Aug. 15, 1977, abandoned, which, in turn, is a continuation-in-part of Ser. No. 779,886, filed Mar. 21, 1977, also abandoned.

This invention relates to novel esters and thiolesters of amino acids, novel intermediates therefor, synthesis thereof and the use of said esters and thiolesters and compositions containing said esters or thiolesters for the control of pests.

The esters and thiolesters of amino acids of the present invention are represented by the following generic formula (A):

$$\begin{array}{c} R^1 \quad R^3 \quad O \\ \diagdown \quad | \quad \| \\ N-C-C-WR^5 \\ \diagup \quad | \\ R^2 \quad R^4 \end{array} \quad (A)$$

wherein,

W is oxygen or sulfur;
$R^1$ is cycloalkyl, cycloalkenyl, cycloalkenyl substituted with halo or lower alkyl, or the group

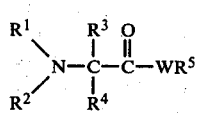

in which t is zero, one, two, three or four; Y is independently selected from hydrogen, lower alkyl, lower haloalkyl, lower alkoxy, lower alkylthio, lower alkylcarbonyl, lower alkoxycarbonyl, lower aryloxy, halogen, cyano, nitro, and lower haloalkylthio; and Z is independently selected from the values of Y, cycloalkyl, and lower haloalkoxy; or Y and Z form a methylenedioxy group;
$R^2$ is hydrogen, lower alkyl, lower haloalkylcarbonyl, or formyl;
$R^3$ is lower alkyl of 2 to 5 carbon atoms, lower alkenyl of 2 to 5 carbon atoms, lower haloalkyl of 1 to 4 carbon atoms, lower haloalkenyl of 2 to 4 carbon atoms, or lower cycloalkyl of 3 or 4 carbon atoms;
$R^4$ is hydrogen or fluoro; and
$R^5$ is a group selected from:

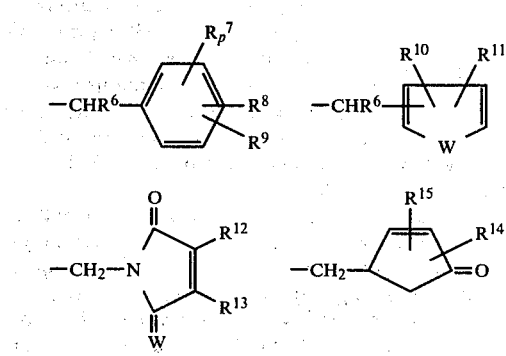

-continued

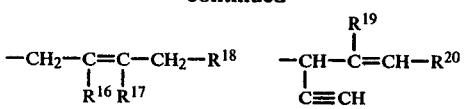

wherein,
p is zero, one, two or three;
$R^6$ is hydrogen, cyano, methyl, trifluoromethyl, ethynyl, or

$R^7$ is halogen, lower alkyl, lower haloalkyl, lower alkoxy, lower haloalkoxy, lower alkylthio, lower alkenyl, or lower haloalkenyl;
$R^8$ is hydrogen or together with $R^7$ forms a lower alkylenedioxy bridge across adjacent ring carbon atoms;
$R^9$ is hydrogen, lower alkenyloxy, lower alkynyl, lower alkynyloxy, lower haloalkynyl, lower alkylcarbonyl, arylcarbonyl, substituted arylcarbonyl, aryloxy, substituted aryloxy, arylthio, substituted arylthio, aralkyl, substituted aralkyl, cycloalkyl, cycloalkalkyl, lower acyloxy, aryloxycarbonyl, lower alkoxycarbonyl, or lower haloalkenyloxy;
$R^{10}$ is hydrogen or lower alkyl;
$R^{11}$ is lower alkenyl, lower alkynyl, or aralkyl;
$R^{12}$ and $R^{13}$ taken together form a lower alkylene or a lower alkenylene bridge;
$R^{14}$ is hydrogen, lower alkyl, lower alkenyl, lower alkynyl, or aralkyl;
$R^{15}$ is hydrogen or lower alkyl;
$R^{16}$ is hydrogen, chloro, fluoro, or methyl;
$R^{17}$ is hydrogen, chloro, fluoro, methyl, or taken together with $R^{16}$ forms a carbon-carbon bond;
$R^{18}$ is phenyl or phenyloxy;
$R^{19}$ is hydrogen, halogen, methyl, or ethyl;
$R^{20}$ is allyl, propargyl, 3-butenyl, 3-butynyl, phenyl, or benzyl; and the salts thereof of strong inorganic acids or organic acids.

The compounds of the present invention represented by generic formula (A) are useful agents for the control of pests such as insects and acarids. Without any intention of being bound by theory and although the mode of action of the compounds of formula (A) as applied to the control of insects and acarids is not completely understood, the compounds of formula (A) appear to be effective for the control of insects and acarids by reason of mechanisms of the nature of the insect control agents known as pyrethrins and synthetic pyrethroids. As such, the organic moiety ($R^5$) may be selected from the organo groups generally associated with the formation of pyrethrin esters and synthetic pyrethroid esters. Typical of such organo groups ($R^5$) are the groups shown in, for example, U.S. Pat. Nos. 3,973,035, 3,973,036, 3,996,244 and 4,003,945, Offenlegungsschrift 26 47 366, and Republic of South Africa Application No. 76/4622, the disclosures of which are incorporated herein by reference.

In the description hereinafter and the appended claims, each of $R^1$ through $R^{20}$, W, Y, Z, p, and t is as defined hereinabove, unless otherwise specified.

As a generally applicable method of synthesis, the compounds of formula (A) can be prepared by the reaction of a primary or secondary amine of formula (I) with a halo ester or thiolester of formula (II) (X is bromo, chloro, or iodo).

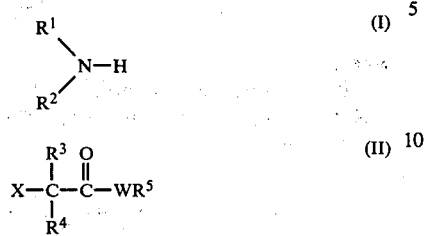

The reaction of an amine (I) and halo ester (II) is generally carried out neat or in an organic solvent such as hexamethylphosphoric triamide, tetrahydrofuran, dimethylformamide, dimethylsulfoxide, or the like at room temperature or above. The reaction generally proceeds rather slowly. It may be assisted by a catalyst such as a small amount of potassium iodide. A good review of the synthesis of amino acids and esters of amino acids is given in "Methodicum Chimicum," Academic Press, New York, Vol. 6, pp 599–623 (1975).

The halo esters of formula II can be prepared from the acid halide thereof (II, wherein $WR^5$ represents bromo or chloro) by reaction with an alcohol ($R^5$—OH). The α-halo-substituted acid halide and α-halo-substituted acid can be prepared by halogenation, using molecular halogen, of (1) a mono-carboxylic acid, or (2) a malonic ester followed by saponification using, for example, the Hell-Volhard-Zelinsky reaction and procedures described in Org. Syn. Coll., Vol. 2, 93 (1943); ibid., Vol. 3, 495, 523, 623, and 848 (1955); ibid., Vol. 4, 358 and 608 (1963); Org. Syn. 50, 31 (1970); and JACS 91, 7090 (1969). Other suitable methods include the reaction of N-bromosuccinimide or N-chlorosuccinimide with an acid halide (II, wherein $WR^5$ represents bromo or chloro) following the procedure of Harpp et al., J. Org. Chem. 40, 3420 (1975) and references cited therein. A method suitable wherein olefinic unsaturation is present in alkylation of acetoacetates followed by halogenation of the anion, e.g. the sodium enolate, and deacetylation. Rathke et al., Tetrahedron Letters, No. 43, 3995 (1971) and Slotter et al., ibid., No. 40, 4067 (1972). The synthesis of α-chloro acids may be accomplished also by reacting the acid with molecular chlorine in the presence of chlorosulfonic acid and chloranil as described by Ogata et al., J. Org. Chem. 40, 2960 (1975). They may also be prepared from α-hydroxy acids by conventional methods.

The compounds of formula (A) can be synthesized also by reacting an acid of formula (III), or the acid chloride or bromide thereof, with an alcohol or mercaptan $HW-R^5$.

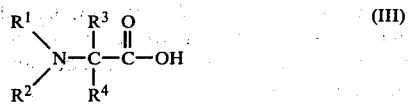

The acid of formula (III) can be made from the halo acid or lower alkyl ester of formula (IV) ($R^{21}$ is hydrogen or lower alkyl) using the conditions described hereinabove by reaction with the amine of formula (I).

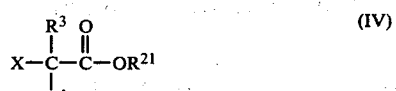

Following reaction of a halo ester of formula (IV) wherein $R^{21}$ is lower alkyl with an amine of formula (I), the resulting amino ester of formula (V)

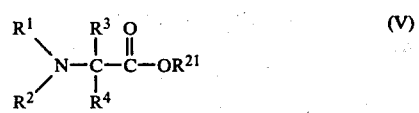

is saponified by conventional methods to the amino acid of formula (III) or a reactive derivative thereof such as the acid chloride, acid bromide or an inorganic salt thereof such as the sodium or potassium salt.

The following terms, wherever used in the description herein and the appended claims, have the meaning defined below, unless otherwise specified hereinafter.

The term "lower alkyl" refers to an alkyl group, straight or branched, having a chain length of one to eight carbon atoms. The term "lower haloalkyl" refers to an alkyl group substituted with one to three halogen atoms such as chloromethyl, fluoromethyl, trifluoromethyl, 2,2,2-trifluoroethyl, 6-chlorohexyl, 2-fluoroethyl, and the like. The term "lower alkoxy" refers to an alkoxy group, straight or branched, having a chain length of one to eight carbon atoms. The term "lower alkylthio" refers to an alkylthio group, straight or branched, having a chain length of one to eight carbon atoms.

The term "lower alkenyl" refers to an ethylenically unsaturated hydrocarbon group, straight or branched, having a chain length of two to eight carbon atoms and one or two ethylenic bonds such as vinyl, allyl, 3-butenyl, 2-hexenyl, i-propenyl, 2,4-hexadienyl, and the like. The term "lower haloalkenyl" refers to a lower alkenyl group substituted with one to three halogen atoms. The term "lower alkenyloxy" refers to an alkenyloxy group, straight or branched, of two to eight carbon atoms. The term "lower haloalkenyloxy" refers to a lower alkenyloxy group substituted with one to three halogen atoms.

The term "lower alkynyl" refers to an alkynyl group, straight or branched, having a chain length of two to eight carbon atoms and one or two acetylenic bonds. The term "lower haloalkynyl" refers to a lower alkynyl group having one to three halogen atoms. The term "lower alkynyloxy" refers to an alkynyloxy group, straight or branched, of three to eight carbon atoms.

The term "cycloalkyl" refers to a cycloalkyl group of three to eight cyclic carbon atoms. The term "cycloalkalkyl" refers to a cycloalkyl group wherein one hydrogen atom is replaced by a lower alkyl group, the total number of carbon atoms being from four to twelve, such as cyclopropanemethyl, cyclobutaneethyl, cyclohexanemethyl, and the like.

The term "aryl" refers to the aryl group phenyl or naphthyl. The term "aralkyl" refers to a lower alkyl group in which a hydrogen atom of the alkyl group is substituted by an aryl group, the total number of carbon atoms being from seven to twelve, such as benzyl, phenethyl, and the like. The terms "substituted aryl" and "substituted aralkyl" refer to an aryl group and an aralkyl group, respectively, substituted at one, two or three of the ring carbon atoms with a group selected from lower alkyl, lower haloalkyl, lower alkoxy, lower alkenyl, lower haloalkenyl, lower alkenyloxy, halogen, nitro, cyano, lower alkylthio, and the like.

The term "lower haloalkoxy" refers to a lower alkoxy group substituted with one to three halogen atoms.

The term "lower acyloxy" refers to a lower organic acyloxy group of one to six carbon atoms, such as acetoxy.

The compounds of the present invention of formula (A) have one or more asymmetric carbon atoms. The present invention includes each of the optical isomers and racemic mixtures thereof. In the examples hereinafter, unless otherwise specified, the compound prepared is a racemic mixture.

Included within the present invention are salts of the compounds of formula A. The salts are formed from strong inorganic acids or organic acids such as hydrochloric acid, sulfuric acid, phosphoric acid, p-toluenesulfonic acid, p-benzenesulfonic acid, methanesulfonic acid, Lewis acid and the like. Many of the compounds of formula A are oils which advantageously are converted into the salt for convenience of handling and formulating and superior stability. The salts are useful for the control of pests in the same way as the compounds of formula A.

The compounds of the present invention of formula A are useful pest control agents, particularly for the control of insects and acarids. In the use of the compounds of formula A for combating insects and acarids for the protection of agricultural crops, for example soybeans, cotton, alfalfa, etc., a compound of formula A, or mixtures thereof, together with a carrier is applied to the locus in a pesticidally effective amount. The carrier can be liquid or solid and include adjuvants such as wetting agents, dispersing agents and other surface active agents. The compounds of formula A can be used in formulations such as wettable powders, solutions, dusts, granules, emulsifiable concentrates, and the like. Suitable solid carriers include natural and synthetic silicates and clays, carbon or charcoal granules, natural and synthetic resins, waxes, and the like. Suitable liquid carriers include water, aromatic hydrocarbons, alcohols, vegetable and mineral oils, ketones, and the like. The amount of a compound of formula A in the formulation can vary widely, generally within the range of about 0.01 percent to about 90.0 percent, by weight.

As shown hereinafter, the compounds of the present invention are effective on many different insects and on acarids. The compounds are effective control agents for insects such as mosquitoes, flies, aphids, weevils and acarids such as the spider mite and ticks. Depending upon the particular combination of the substituents of formula A herein, the compounds have a broad or relatively narrow spectrum of unusually high pesticidal activity on insects and acarids. Among the pests against which the compounds of the present invention are pesticidally effective are insects of the order Lepidoptera, Orthoptera, Heteroptera, Homoptera, Diptera, Coleoptera or Hymenoptera, and acarids of the order Acarina including mites of the family Tetranychidae or Tarsonemidae and ticks such as Ornithodoros.

The compounds of the present invention can be used in combination with other pesticides such as the carbamates, phosphates and insect growth regulators, e.g. propoxur, carbaryl, naled, dichlorvos, methoprene, kinoprene, hydroprene, cyhexatin and resmethrin.

The following examples are provided to illustrate the practice of the present invention. Temperature is given in degrees Centigrade. RT means room temperature.

EXAMPLE 1

A. To α-bromoisovaleric acid (10 g, 0.055 mole) in 60 ml ether, cooled to 10°, is added dimethylformamide (DMF) (2.8 ml, 0.0332 mole), followed by slow addition of thionylchloride (5.9 ml, 0.0828 mole). After about one hour at 24°, the acid chloride intermediate is isolated by decanting off the top ether layer from the oily residue and removing the ether under vacuum. To the acid chloride (0.055 mole) in 100 ml of ether, cooled to 10°, is added m-phenoxybenzyl alcohol (11.49 g, 0.0495 mole) followed by addition of pyridine (9 ml, 0.11 mole) over about 15 minutes. The resulting white slurry is stirred at 24° for about 16 hours and then a trace of water is added to decompose excess acid chloride. The ester is isolated by pouring reaction slurry into ice water (100 ml), acidifying with 2 N sulfuric acid (60 ml) and extracting with ether (3×100 ml). The combined ether extracts are washed with 10% sodium bicarbonate (10 ml), followed by water (2×100 ml) and brine (25 ml) and dried over calcium sulfate to give m-phenoxybenzyl α-bromoisovalerate in quantitative yield.

NMR (CCl₄) δ1.03 [m, 6, (CH₃)₂CH], 2.18 [m, 6, (CH₃)₂CH],

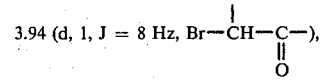

3.94 (d, 1, J = 8 Hz, Br—CH—C—), and 5.11 ppm (s, 2, ArCH₂O—). IR (film) 1744 cm⁻¹ (C=O).

B. To m-phenoxybenzyl α-bromoisovalerate (3 g, 0.0083 mole) in 6 ml of hexamethylphosphorictriamide (HMPT), 24°, is added aniline (0.0248 mole) followed by a catalytic amount of potassium iodide (28 mg). The reaction mixture is heated, at 65°, for about 90 hours and then poured into ice-water (35 ml) and extracted with ether (3×50 ml). The combined ether extracts are washed with 2 N sulfuric acid, water (2×50 ml) until neutral, and with brine followed by drying over calcium sulfate. The product is concentrated under vacuum and isolated by preparative thin layer chromatography (TLC). m-Phenoxybenzyl ester of N-phenylvaline.

NMR (CDCl₃) δ1.00 [m, 6, CH₃)₂CH], 2.07 [m, 1, (CH₃)₂—CH],

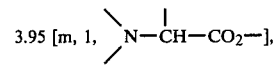

3.95 [m, 1, N—CH—CO₂—], 4.00 (m, 1, NH), and 5.13 ppm (s, 2, ArCH₂O). IR (film) 3400 cm⁻¹ (s) (NH) and 1738 cm⁻¹ (C=O).

EXAMPLE 2

To the m-phenoxybenzyl ester of N-phenylvaline (0.25 g) in HMPT (1 ml) and tetrahydrofuran (1 ml), at 24°, is added methyl iodide (0.12 ml) followed by potassium carbonate (0.092 g). The reaction mixture is heated at 60° for 4 days. The reaction is worked up by pouring into ice-water (5 ml) and extracting with ether (3×10 ml). The combined ether extracts are washed with water (2×10 ml) and brine (1×5 ml) and dried over calcium sulfate. The product is isolated and purified by preparative TLC to give the m-phenoxybenzyl ester of N-phenyl-N-methylvaline.

NMR (CDCl$_3$) δ0.92 [m, 6, (C$\underline{H}$$_3$)$_2$CH], 2.3 [m, 1, (CH$_3$)$_2$— C$\underline{H}$], 2.88 (s, 3, C$\underline{H}$$_3$N),

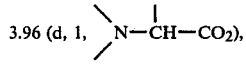

3.96 (d, 1, and 5.08 ppm (s, 2, ArC$\underline{H}$$_2$O). IR (film) 1740 (C=O).

EXAMPLE 3

A. To valine (11.7 g, 0.10 mole) in 88% formic acid (40 ml) is added acetic formylanhydride (26.3 g, 0.30 mole) over 0.5 hr at 5°. The reaction mixture is warmed to 24° and stirred for 17 hours. The reaction is worked up by distilling off (bath temp. 45°-50°) the solvent, excess anhydride and acetic acid, to give, as a white solid, N-formylvaline, recrystallized from hot ethanol, m.p. 143°-145°.

B. To 8 g (0.055 mole) of the product of part A in 55 ml of HMPT is added m-phenoxybenzyl bromide (14.4 g, 0.055 mole) followed by anhydrous potassium carbonate (7.6 g, 0.055 mole). The reaction mixture is stirred, at 24°, for 48 hours and then worked up by pouring into ice-water (250 ml) and extracting with ether (3×100 ml). The combined ether extracts are washed with water (2×100 ml) and brine (25 ml) and dried over calcium sulfate and evaporated under vacuum to give the m-phenoxybenzyl ester of N-formylvaline.

C. To the ester (26 g, 0.0835 mole) of part B, in 84 ml of anhydrous methanol, is added 1 N methanolic HCl (92 ml, 0.092 mole). The reaction mixture is stirred at 24° for 18 hours and then the methanol removed under vacuum. The residue is poured into ice-water (200 ml) followed by removal of neutral impurities with ether. The aqueous layer is made basic by addition of 10% sodium bicarbonate and then extracted with ether (3×200 ml). The combined ether phases are washed with water (2×200 ml) until neutral and brine (100 ml) and then dried over calcium sulfate, filtered and rotoevaporated to give the m-phenoxybenzyl ester of valine.

NMR (CDCl$_3$) δ0.91 [m, 6, (C$\underline{H}$$_3$)$_2$CH], 1.37 (bs, 2, NH$_2$), 2.00 [m, 1, (CH$_3$)$_2$C$\underline{H}$],

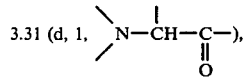

3.31 (d, 1, and 5.17 ppm (s, 2, ArC$\underline{H}$$_2$O—). IR (film) ~3400 cm$^{-1}$ (NH$_2$), 1740 cm$^{-1}$ (C=O).

EXAMPLE 4

To m-phenoxybenzyl α-bromoisovalerate (5 g, 0.0138 mole) in 9 ml of HMPT, at 24°, is added p-chloroaniline (5.27 g, 0.0413 mole) and a catalytic amount of potassium iodide (60 mg). The reaction mixture is stirred at 70° for four days. The reaction is then poured into ice-water (30 ml) and 10 ml of 2 N sulfuric acid which is extracted with ether (3×30 ml). The combined ether extracts are washed with water (2×30 ml) and brine (10 ml), dried over calcium sulfate, filtered and evaporated. The crude product is purified by preparative TLC to yield the m-phenoxybenzyl ester of N-(p-chlorophenyl)valine.

NMR (CDCl$_3$) δ0.99 [m, 6, (C$\underline{H}$$_3$)$_2$CH], 2.03 [m, 1, (CH$_3$)$_2$C$\underline{H}$],

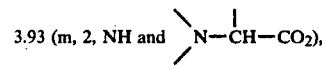

3.93 (m, 2, NH and and 5.10 ppm (s, 2, ArC$\underline{H}$$_2$O—). IR (film) 3410 cm$^{-1}$ (s) (NH), and 1740 cm$^{-1}$ (C=O).

EXAMPLE 5

To m-phenoxybenzyl α-bromoisovalerate (2 g, 0.0055 mole) in 4 ml of HMPT, at 24°, is added toluidine (1.77 g, 0.0165 mole) and potassium iodide (25 mg). The reaction mixture is stirred at 60° for five days, cooled, and poured into ice-water (20 ml) plus 10 ml of 2 N sulfuric acid. The reaction is worked up as in Example 4 yielding the m-phenoxybenzyl ester of N-(p-methylphenyl)-valine.

NMR (CDCl$_3$) δ0.99 [m, 6, (C$\underline{H}$$_3$)$_2$CH], 2.20 (s, 3, C$\underline{H}$$_3$—Ar),

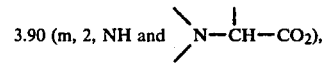

3.90 (m, 2, NH and and 5.11 ppm (s, 2, ArC$\underline{H}$$_2$O). IR (film) 3400 cm$^{-1}$ (s) (NH), and 1740 cm$^{-1}$ (C=O).

The above procedure is repeated using anisdine in place of toluidine to yield the m-phenoxybenzyl ester of N-(p-methoxyphenyl)valine.

NMR (CDCl$_3$) δ0.98 [m, 6, (C$\underline{H}$$_3$)$_2$CH], 2.03 [m, 1, (CH$_3$)$_2$C$\underline{H}$], 3.73 (s, 3, OC$\underline{H}$$_3$),

3.77 (m, 2, NH and and 5.10 ppm (s, 2, ArC$\underline{H}$$_2$O—). IR (film) 3400 cm$^{-1}$ (s) (NH), and 1740 cm$^{-1}$ (C=O).

EXAMPLE 6

A. To α-bromoisovaleric acid (5.18 g, 0.0286 mole) in 30 ml of ether, cooled to 10°, is added 1.3 ml of DMF followed by slow addition of 3 ml of thionyl chloride (0.0429 mole). After one hour at 24°, the acid chloride is isolated in quantitative yield by decanting off top the ether layer and removing the solvent and excess thionyl chloride under vacuum.

To the acid chloride (5.7 g, 0.0286 mole) in 30 ml of ether at 10° is added 5.38 g of m-phenoxybenzaldehyde cyanohydrin (0.0257 mole) followed by slow addition of 4.6 ml of pyridine over 10 minutes. The reaction mixture is stirred at 24° for 17 hours and then a trace of water is added to destroy excess acid chloride. The reaction product is worked up by pouring into ice-water (50 ml) plus 2 N sulfuric acid (30 ml) and extracting with ether (3×30 ml). The combined ether extracts are washed with 10% sodium bicarbonate (10 ml), water (2×50 ml) and brine (10 ml), dried over calcium sulfate and evaporated to yield m-phenoxy-α-cyanobenzyl α-bromoisovalerate.

NMR (CDCl₃) δ1.05 [m, 6, (C$\underline{H}$₃)₂CH], 2.23 [m, 1, (CH₃)₂C$\underline{H}$],

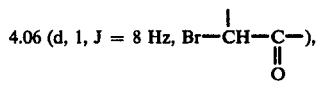

4.06 (d, 1, J = 8 Hz, Br—CH—C—),
                                 ‖
                                 O and 6.41 ppm [s, 1, ArC$\underline{H}$(CN)O]. IR (film) 1762 cm⁻¹ (C=O).

B. To m-phenoxy-α-cyanobenzyl α-bromoisovalerate (2.0 g, 0.0052 mole) in 4 ml of HMPT, at 24°, is added aniline (1.5 g, 0.016 mole) and potassium iodide (21 mg). The reaction is stirred at 65° for 90 hours and then cooled and poured into ice-water (20 ml) plus 2 N sulfuric acid (10 ml). The reaction is worked up as in Example 4 and purified by preparative TLC to give the m-phenoxy-α-cyanobenzyl ester of N-phenylvaline.

NMR (CDCl₃) δ1.02 (m, 6, (CH₃)₂CH], 2.10 [m, 1, (CH₃)₂CH],

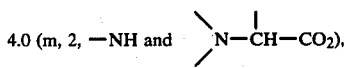

4.0 (m, 2, —NH and  \
                     N—CH—CO₂),
                    / and 6.33 ppm [s, 1, ArCH(CN)O]. IR (film) 3400 cm⁻¹ (s) (NH), 2260 cm⁻¹ (w) (C≡N), 1758 cm⁻¹ (C=O).

EXAMPLE 7

Following the procedure of Example 5, each of the compounds under column I is reacted with m-phenoxybenzyl α-bromoisovalerates to yield the respective ester under column II.

I 3,4,5-trimethoxyaniline
4-phenetidine
2,4-dimethoxyaniline
3,5-dimethoxyaniline
2-anisidine
4-ethylaniline
2,4,6-trimethylaniline
4-nitroaniline
2,4,6-trichloroaniline
4-fluoroaniline
4-bromoaniline
3-chloro-2-methoxyaniline
2-chloro-4-methylaniline
2,6-dichloroaniline
4-chloro-2-nitroaniline
2,6-dichloro-4-nitroaniline
4-aminoacetophenone
3-aminobenzonitrile
2-aminobenzonitrile
2,6-dimethylaniline
2,5-dimethylaniline

II

The m-phenoxybenzyl ester of
N-(3,4,5-trimethoxyphenyl)valine
N-(4-ethoxyphenyl)valine
N-(2,4-dimethoxyphenyl)valine
N-(3,5-dimethoxyphenyl)valine
N-(2-methoxyphenyl)valine
N-(4-ethylphenyl)valine
N-(2,4,6-trimethylphenyl)valine
N-(4-nitrophenyl)valine
N-(2,4,6-trichlorophenyl)valine
N-(4-fluorophenyl)valine
N-(4-bromophenyl)valine
N-(3-chloro-2-methoxyphenyl)valine
N-(2-chloro-4-methylphenyl)valine
N-(2,6-dichlorophenyl)valine
N-(4-chloro-2-nitrophenyl)valine
N-(2,6-dichloro-4-nitrophenyl)valine
N-(4-methylcarbonylphenyl)valine
N-(3-cyanophenyl)valine
N-(2-cyanophenyl)valine
N-(2,6-dimethylphenyl)valine
N-(2,5-dimethylphenyl)valine

EXAMPLE 8

Following the procedure of Example 1, α-bromoisovaleric acid via the acid halide is reacted with the alcohols listed in column III to yield the respective ester under column IV.

III p-phenoxybenzyl alcohol
m-benzylbenzyl alcohol
p-propargylbenzyl alcohol
4-allyl-2,6-dimethylbenzyl alcohol
p-allylbenzyl alcohol
2,6-dimethyl-4-propargylbenzyl alcohol
α-ethynyl-3-trifluoromethylbenzyl alcohol
5-benzyl-3-furylmethyl alcohol
α-cyano-5-benzyl-3-furylmethyl alcohol
5-propargylfurfuryl alcohol
2-methyl-5-propargyl-3-furylmethyl alcohol
5-propargyl-α-ethynylfurfuryl alcohol
5-benzyl-2-methyl-3-furylmethyl alcohol
3-methyl-2-propargyl-2-cyclopentene-1-one-4-ol
2-allyl-3-methyl-2-cyclopentene-1-one-4-ol
2-benzyl-2-cyclopentene-1-one-4-ol
3,4,5,6-tetrahydrophthalimidomethyl alcohol
phthalimidomethyl alcohol
4-methyl-3-chloro-2-butene-1-ol
5-propargyl-2-thiophenemethanol
5-benzyl-2-thiophenemethanol
5-benzyl-3-thiophenemethanol

IV p-phenoxybenzyl α-bromoisovalerate
m-benzylbenzyl α-bromoisovalerate
p-propargyl-benzyl α-bromoisovalerate
4-allyl-2,6-dimethylbenzyl α-bromoisovalerate
p-allylbenzyl α-bromoisovalerate
2,6-dimethyl-4-propargyl-benzyl α-bromoisovalerate
α-ethynyl-3-trifluoromethylbenzyl α-bromoisovalerate
5-benzyl-3-furylmethyl α-bromoisovalerate
α-cyano-5-benzyl-3-furylmethyl α-bromoisovalerate
5-propargylfurfuryl α-bromoisovalerate
2-methyl-5-propargyl-3-furylmethyl α-bromoisovalerate
5-propargyl-α-ethynylfurfuryl α-bromoisovalerate
5-benzyl-2-methyl-3-furylmethyl α-bromoisovalerate
2-methyl-3-propargyl-4-oxo-2-cyclopentene-1-yl α-bromoisovalerate
3-allyl-2-methyl-4-oxo-2-cyclopentene-1-yl α-bromoisovalerate
3-benzyl-4-oxo-2-cyclopentene-1-yl α-bromoisovalerate
3,4,5,6-tetrahydrophthalimidomethyl α-bromoisovalerate phthalimidomethyl α-bromoisovalerate
4-phenyl-3-chloro-2-butene-1-yl α-bromoisovalerate
5-propargyl-2-thiophenemethyl α-bromoisovalerate
5-benzyl-2-thiophenemethyl α-bromoisovalerate
5-benzyl-3-thiophenemethyl α-bromoisovalerate

EXAMPLE 9

Each of the α-bromo ester intermediates listed under column IV is reacted with 4-chloroaniline using the procedure hereinabove, e.g. Example 1, 4 or 5, to yield the respective ester of N-(4-chlorophenyl)valine listed under column V.

V 4-phenoxybenzyl ester of N-(4-chlorophenyl)valine
3-benzylbenzyl ester of N-(4-chlorophenyl)valine
4-propargylbenzyl ester of N-(4-chlorophenyl)valine
4-allyl-2,6-dimethylbenzyl ester of N-(4-chlorophenyl)valine
p-allylbenzyl ester of N-(4-chlorophenyl)valine
2,6-dimethyl-4-propargylbenzyl ester of N-(4-chlorophenyl)valine
α-ethynyl-3-trifluoromethylbenzyl ester of N-(4-chlorophenyl)valine
5-benzyl-3-furylmethyl ester of N-(4-chlorophenyl)valine
α-cyano-5-benzyl-3-furylmethyl ester of N-(4-chlorophenyl)valine
5-propargylfurfuryl ester of N-(4-chlorophenyl)valine
2-methyl-5-propargyl-3-furylmethyl ester of N-(4-chlorophenyl)valine
5-propargyl-α-ethynylfurfuryl ester of N-(4-chlorophenyl)valine
5-benzyl-2-methyl-3-furylmethyl ester of N-(4-chlorophenyl)valine
2-methyl-3-propargyl-4-oxo-2-cyclopentene-1-yl ester of N-(4-chlorophenyl)valine
3-allyl-2-methyl-4-oxo-2-cyclopentene-1-yl ester of N-(4-chlorophenyl)valine
3-benzyl-4-oxo-2-cyclopentene-1-yl ester of N-(4-chlorophenyl)valine
3,4,5,6-tetrahydrophthalimidomethyl ester of N-(4-chlorophenyl)valine
phthalimidomethyl ester of N-(4-chlorophenyl)valine
4-phenyl-3-chloro-2-butene-1-yl ester of N-(4-chlorophenyl)valine
5-propargyl-2-thiophenemethyl ester of N-(4-chlorophenyl)valine
5-benzyl-2-thiophenemethyl ester of N-(4-chlorophenyl)valine
5-benzyl-3-thiophenemethyl ester of N-(4-chlorophenyl)valine

EXAMPLE 10

Following the procedure of Example 5, each of the amino compounds listed under column VI is reacted with m-phenoxybenzyl α-bromoisovalerate to yield the respective N-substituted ester listed under column VII.

VI 2-chloro-6-methylaniline
4-chloro-2-methylaniline
4-chloro-3-trifluoromethylaniline
2-chloro-5-trifluoromethylaniline
2-trifluoromethylaniline
3-trifluoromethylaniline
3,5-dichloro-4-hydroxyaniline
4-chloro-3-nitroaniline
2,3-dichloroaniline
2-fluoroaniline
2,6-diiodo-4-nitroaniline
3,4,5-trichloroaniline
4-ethoxycarbonylaniline
2-nitroaniline
3-nitroaniline
4-(n-butyl)aniline
4-cyclopropylaniline
2,3-dimethylaniline
4-isopropylaniline
3,5-dimethylaniline
2,4-dimethylaniline
4-hydroxyaniline
2-methylthioaniline
2,5-dichloraniline
3,4-methylenedioxyaniline
3,4-dimethoxyaniline
2,6-difluoroaniline
3,4-dichloroaniline

VII

The m-phenoxybenzyl ester of
N-(2-chloro-6-methylphenyl)valine
N-(4-chloro-2-methylphenyl)valine
N-(4-chloro-3-trifluoromethylphenyl)valine
N-(2-chloro-5-trifluoromethylphenyl)valine
N-(2-trifluoromethylphenyl)valine
N-(3-trifluoromethylphenyl)valine
N-(3,5-dichloro-4-hydroxyphenyl)valine
N-(4-chloro-3-nitrophenyl)valine
N-(2,3-dichlorophenyl)valine
N-(2-fluorophenyl)valine
N-(2,6-diiodo-4-nitrophenyl)valine
N-(3,4,5-trichlorophenyl)valine
N-(4-ethoxycarbonylphenyl)valine
N-(2-nitrophenyl)valine
N-(3-nitrophenyl)valine
N-(4-n-butylphenyl)valine
N-(4-cyclopropylphenyl)valine
N-(2,3-dimethylphenyl)valine
N-(4-isopropylphenyl)valine
N-(3,5-dimethylphenyl)valine
N-(2,4-dimethylphenyl)valine
N-(4-hydroxyphenyl)valine
N-(2-methylthiophenyl)valine
N-(2,5-dichlorophenyl)valine
N-(3,4-methylenedioxyphenyl)valine
N-(3,4-dimethoxyphenyl)valine
N-(2,6-difluorophenyl)valine
N-(3,4-dichlorophenyl)valine

EXAMPLE 11

The α-halo acid chloride listed in column VIII is reacted with m-phenoxybenzyl alcohol to prepare the respective α-halo ester in column IX according to procedures hereinabove such as Example 1.

VIII 2-bromo-3-methylpentanoyl chloride
2-bromo-4-methylpentanoyl chloride
2-bromobutanoyl chloride
2-bromohexanoyl chloride
2-bromo-3-chloropropanoyl chloride
2,5-dichloropentanoyl chloride
2-chloro-4-trichloromethylbutanoyl chloride

IX 3-phenoxybenzyl 2-bromo-3-methylpentanoate
3-phenoxybenzyl 2-bromo-4-methylpentanoate
3-phenoxybenzyl 2-bromobutanoate
3-phenoxybenzyl 2-bromohexanoate
3-phenoxybenzyl 2-bromo-3-chloropropionate
3-phenoxybenzyl 2,5-dichloropentanoate
3-phenoxybenzyl 2,4,4,4-tetrachlorobutanoate Following the procedures hereinabove such as Example 4, 4-chloroaniline is reacted with each of the α-halo esters listed in column IX to yield the respective substituted amino ester of column X.

X 3-phenoxybenzyl ester of N-(4-chlorophenyl)isoleucine
3-phenoxybenzyl ester of N-(4-chlorophenyl)leucine
3-phenoxybenzyl ester of 2-(4-chlorophenylamino)-butanoic acid
3-phenoxybenzyl ester of 2-(4-chlorophenylamino)hexanoic acid
3-phenoxybenzyl ester of 2-(4-chlorophenylamino)-3-chloropropionic acid
3-phenoxybenzyl ester of 2-(4-chlorophenylamino)-5-chloropentanoic acid
3-phenoxybenzyl ester of 2-(4-chlorophenylamino)-4,4,4-trichlorobutanoic acid

EXAMPLE 12

To the m-phenoxybenzyl ester of valine (2 g, 0.0067 mole) in methanol (30 ml) is added concentrated sulfuric acid to bring to about pH 6. Cyclohexanone (0.6 g, 0.006 mole) is then added followed by 3 A molecular sieves and sodium cyanoborohydride (0.25 g, 0.004 mole). Additional sulfuric acid is added to keep pH at about 6. After about 24 hours, the reaction is worked up by removing methanol by rotoevaporation and the residue is poured into water and 10% sodium carbonate followed by extraction with ether. The combined ether extracts are filtered and concentrated and the product is isolated by preparatory TLC (10% ether/hexane) to yield the m-phenoxybenzyl ester of N-cyclohexylvaline.

NMR (CDCl$_3$) δ0.89 [m, 6, J-7 Hz, (C$\underline{H}_3$)$_2$CH], 2.26 [m, 1, (CH$_3$)$_2$C$\underline{H}$],

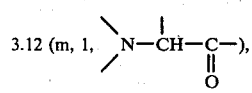
3.12 (m, 1, \N—CH—C—),
              /      ‖
                     O and 5.15 ppm (s, ArC$\underline{H}_2$O), IR (film) 1736 cm$^{-1}$ (C=O).

EXAMPLE 13

Each of the substituted aryl amines listed in column XI is reacted with m-phenoxybenzyl 2-bromoisovalerate using the procedure of Example 4 to prepare the respective N-substituted compound in column XII.

XI 2,4-dichloroaniline
3-methoxyaniline
3,4-dimethylaniline
2,3,5,6-tetrachloroaniline
3-methylaniline
3,5-dichloroaniline
3-acetoaniline
2-acetoaniline
2-methylaniline

XII m-phenoxybenzyl ester of
N-(2,4-dichlorophenyl)valine
N-(3-methoxyphenyl)valine
N-(3,4-dimethylphenyl)valine
N-(2,3,5,6-tetrachlorophenyl)valine
N-(3-methylphenyl)valine
N-(3,5-dichlorophenyl)valine
N-(3-acetophenyl)valine
N-(2-acetophenyl)valine
N-(2-methylphenyl)valine

EXAMPLE 14

Following the process of Example 1, each of the alcohols listed in column XIII is reacted with the acid chloride of α-bromoisovaleric acid to yield the respective ester in column XIV.

XIII 3-(2,2-dichlorovinyloxy)benzyl alcohol
3-(o-fluorophenoxy)benzyl alcohol
4-phenyl-2-butenyl alcohol
4-(4-methylphenoxy)-2-butynyl) alcohol
4-(4-methylphenyl)-2-butenyl alcohol
3-phenylcarbonylbenzyl alcohol
1-ethynyl-2-methyl-2,5-hexadien-1-yl alcohol
1-ethynyl-2-methyl-2-penten-1-yl alcohol
1-ethynyl-2-methyl-3-phenyl-2-propen-1-yl alcohol
1-ethynyl-3-phenyl-2-propen-1-yl alcohol
2,4,6-trimethylbenzyl alcohol

XIV 3-(2,2-dichlorovinyloxy)benzyl α-bromoisovalerate
3-(o-fluorophenoxy)benzyl α-bromoisovalerate
4-phenyl-2-butenyl α-bromoisovalerate
4-(4-methylphenoxy)-2-butynyl α-bromoisovalerate
4-(4-methylphenyl)-2-butenyl α-bromoisovalerate
3-phenylcarbonylbenzyl α-bromoisovalerate
α-ethynyl-2-methyl-2,5-hexadienyl α-bromoisovalerate
α-ethynyl-2-methyl-2-pentenyl α-bromoisovalerate
α-ethynyl-2-methyl-3-phenyl-2-propenyl α-bromoisovalerate
α-ethynyl-3-phenyl-2-propenyl α-bromoisovalerate
2,4,6-trimethylbenzyl α-bromoisovalerate Following the procedures hereinabove such as Example 5, p-methylaniline is reacted with each of the α-bromo esters in column XIV to yield the respective ester of N-(p-methylphenyl)valine in column XV.

XV 3-(2,2-dichlorovinyloxy)benzyl ester of N-(p-methylphenyl)valine
3-(o-fluorophenoxy)benzyl ester of N-(p-methylphenyl)valine
4-phenyl-2-butenyl ester of N-(p-methylphenyl)valine
4-(4-methylphenoxy)-2-butynyl ester of N-(p-methylphenyl)valine
4-(4-methylphenyl)-2-butenyl ester of N-(p-methylphenyl)valine
3-phenylcarbonylbenzyl ester of N-(p-methylphenyl)valine
α-ethynyl-2-methyl-2,5-hexadienyl ester of N-(p-methylphenyl)valine α-ethynyl-2-methyl-2-pentenyl ester of N-(p-methylphenyl)valine α-ethynyl-2-methyl-3-phenyl-2-propenyl ester of N-(p-methylphenyl)valine α-ethynyl-3-phenyl-2-propenyl ester of N-(p-methylphenyl)valine 2,4,6-trimethylbenzyl ester of N-(p-methylphenyl)valine

EXAMPLE 15

Each of the α-halo esters in column IX hereinabove is reacted with p-methylaniline to yield the respective 3-phenoxybenzyl ester of the p-methylphenyl amino acid in column XVI using the procedure of Example 5.

XVI 3-phenoxybenzyl ester of N-(p-methylphenyl)isoleucine 3-phenoxybenzyl ester of N-(p-methylphenyl)leucine 3-phenoxybenzyl ester of 2-(p-methylphenylamino)butanoic acid 3-phenoxybenzyl ester of 2-(p-methylphenylamino)hexanoic acid 3-phenoxybenzyl ester of 2-(p-methylphenylamino)-3-chloropropionic acid 3-phenoxybenzyl ester of 2-(p-methylphenylamino)-5-chloropentanoic acid 3-phenoxybenzyl ester of 2-(p-methylphenylamino)-4,4,4-trichlorobutanoic acid

EXAMPLE 16

Each of the α-bromo esters listed in column IV is reacted with p-methylaniline using the procedure of Example 5 to yield the respective ester of N-(p-methylphenyl)valine in column XVII.

XVII 4-phenoxybenzyl ester of N-(p-methylphenyl)valine 3-benzylbenzyl ester of N-(p-methylphenyl)valine 4-propargylbenzyl ester of N-(p-methylphenyl)valine 4-allyl-2,6-dimethylbenzyl ester of N-(p-methylphenyl)valine p-allylbenzyl ester of N-(p-methylphenyl)valine 2,6-dimethyl-4-propargylbenzyl ester of N-(p-methylphenyl)valine α-ethynyl-3-trifluoromethylbenzyl ester of N-(p-methylphenyl)valine 5-benzyl-3-furylmethyl ester of N-(p-methylphenyl)valine α-cyano-5-benzyl-3-furylmethyl ester of N-(p-methylphenyl)valine 5-propargylfurfuryl ester of N-(p-methylphenyl)valine 2-methyl-5-propargyl-3-furylmethyl ester of N-(p-methylphenyl)valine 5-propargyl-α-ethynylfurfuryl ester of N-(p-methylphenyl)valine 5-benzyl-2-methyl-3-furylmethyl ester of N-(p-methylphenyl)valine 2-methyl-3-propargyl-4-oxo-2-cyclopentene-1yl ester of N-(p-methylphenyl)valine 3-allyl-2-methyl-4-oxo-2-cyclopentene-1-yl ester of N-(p-methylphenyl)valine 3-benzyl-4-oxo-2-cyclopentene-1-yl ester of N-(p-methylphenyl)valine 3,4,5,6-tetrahydrophthalimidomethyl ester of N-(p-methylphenyl)valine phthalimidomethyl ester of N-(p-methylphenyl)valine 4-phenyl-3-chloro-2-butene-1-yl ester of N-(p-methylphenyl)valine 5-propargyl-2-thiophenemethyl ester of N-(p-methylphenyl)valine 5-benzyl-2-thiophenemethyl ester of N-(p-methylphenyl)valine 5-benzyl-3-thiophenemethyl ester of N-(p-methylphenyl)valine

EXAMPLE 17

A. Two grams of α-bromoisovaleric acid (0.011 mole) dissolved in 10 ml of methanol is titrated to the phenolphthalein end point at 0° with 2 N sodium hydroxide/methanol. The alcohol is then removed and 10 ml of dimethylformamide and p-trifluoromethylaniline (3.54 g, 0.022 mole) added. The reaction mixture is heated at 100° for 2 hours and left at room temperature about 18 hours. The reaction mixture is poured into 50 ml of 0.1 N sodium hydroxide, washed with ether and the aqueous phase adjusted to pH 4 with conc. HCl and then extracted with chloroform (3×). The extracts are combined and washed with brine, dried, concentrated in a rotoevaporator and solvent removed under vacuum at about 50° to yield N-(p-trifluoromethylphenyl)valine.

B. A mixture of the acid of part A (1.84 g, 0.0071 mole) and potassium carbonate (1.95 g) in 10 ml of dry dimethylformamide is stirred at room temperature, under nitrogen, for 0.5 hours and then m-phenoxybenzyl bromide (1.85 g, 0.0071 mole) is added at 0°. The reaction mixture is allowed to warm up to room temperature and is then stirred about 18 hours. The reaction is then worked up by pouring into ice-water and extracting with ether (3×). The ether extracts are combined and washed with water and brine, dried over calcium sulfate and evaporated under vacuum to yield the m-phenoxybenzyl ester of N-(p-trifluoromethylphenyl)valine. MS m/e 443 (M+, 5.9).

EXAMPLE 18

To a solution of α-bromoisovaleric acid (2 g, 0.110 mole) and 5 ml of methanol is added one drop of phenolphthalein and then sufficient sodium hydroxide/methanol until adjusted to neutral pH. The solvent is then stripped off and p-chloroaniline (7 g, 0.055 mole) added. The mixture is melted in a 100° bath and stirred at 100° for 3 hours. The mixture is cooled and taken up in ether, and 10% aqueous sodium hydroxide is added. The aqueous phase is acidified to pH 4 and extracted with ether. The ether extracts are combined and washed with brine, dried over sodium sulfate and stripped to yield N-(p-chlorophenyl)valine.

Following the procedure of Example 1, part A, N-(p-chlorophenyl)valine is converted to the acid chloride and then reacted with m-phenoxybenzyl alcohol to yield the m-phenoxybenzyl ester of N-(p-chlorophenyl)valine.

EXAMPLE 19

Following the procedure of Example 17, N-(2-fluoro-4-chlorophenyl)valine (0.79 g) is reacted with α-ethynyl-m-phenoxybenzyl bromide (0.39 g) to yield the α-ethynyl-m-phenoxybenzyl ester of N-(2-fluoro-4-chlorophenyl)valine, MS m/e 451 (M+). N-(2-fluoro-4-chlorophenyl)valine is prepared from 2-fluoro-4-chloroaniline and α-bromoisovaleric acid using the procedure of Example 17.

EXAMPLE 20

Following the procedure of Example 5, m-phenoxybenzyl α-bromoisovalerate is reacted with each of the substituted phenyl amines in column XVIII to prepare the respective N-substituted valine in column XIX.

XVIII 4-chloro-3-methylaniline
4-bromo-3-methylaniline
3-bromo-4-methylaniline
3,4-dibromoaniline
3-bromo-4-chloroaniline
4-(t-butyl)aniline
4-nitro-3-trifluoromethylaniline
3,5-di(trifluoromethyl)aniline

XIX m-Phenoxybenzyl ester of
N-(4-chloro-3-methylphenyl)valine
N-(4-bromo-3-methylphenyl)valine
N-(3-bromo-4-methylphenyl)valine
N-(3,4-dibromophenyl)valine
N-(3-bromo-4-chlorophenyl)valine
N-(4-t-butylphenyl)valine
N-(4-nitro-3-trifluoromethylphenyl)valine
N-(3,5-ditrifluoromethylphenyl)valine

EXAMPLE 21

Following the procedure of Example 1, each of m-(p-chlorophenoxy)benzyl alcohol, m-(p-methylphenoxy)benzyl alcohol, and m-(m-trifluoromethylphenoxy)benzyl alcohol is reacted with α-bromoisovaleric acid chloride to yield:

m-(p-chlorophenoxy)benzyl α-bromoisovalerate;
m-(p-methylphenoxy)benzyl α-bromoisovalerate; and
m-(m-trifluoromethylphenoxy)benzyl α-bromoisovalerate.

Each of the above α-bromo esters is reacted with p-methylaniline to yield:

m-(p-chlorophenoxy)benzyl ester of N-(p-methylphenyl)valine;
m-(p-methylphenoxy)benzyl ester of N-(p-methylphenyl)valine; and
m-(m-trifluoromethylphenoxy)benzyl ester of N-(p-methylphenyl)valine.

EXAMPLE 22

To m-phenoxybenzyl α-bromoisovalerate (2 g, 0.0055 mole), 24°, is added 2,6-dimethylaniline (3.33 g, 0.0275 mole) followed by a catalytic amount of potassium iodide (20 mg). The reaction mixture is heated at about 120° for 48 hours, and then poured into ice-water (20 ml) and 2 N sulfuric acid (10 ml) and extracted with ether (3×30 ml). The combined ether extracts are washed with water (2×20 ml) until neutral and with brine (10 ml) followed by drying over calcium sulfate. The reaction product is concentrated under vacuum and isolated by preparative TLC to give m-phenoxybenzyl ester of N-(2,6-dimethylphenyl)valine. MS m/e 403.2 (M+, 7.5).

EXAMPLE 23

To m-phenoxybenzyl α-bromoisovalerate (2 g, 0.0055 mole), 24°, is added 2-methylaniline (2.95 g, 0.0275 mole) followed by a catalytic amount of potassium iodide (20 mg). The reaction mixture is heated, 110°–115°, for about 36 hours, and then poured into ice-water (30 ml) and 2 N sulfuric acid (10 ml) and extracted with ether (3×30 ml). The combined ether extracts are washed with water (2×30 ml) until neutral and with brine (10 ml) followed by drying over calcium sulfate. The reaction product is concentrated under vacuum and isolated by preparative TLC to yield 3-phenoxybenzyl ester of N-(2-methylphenyl)valine. MS m/e 389.2 (M+).

EXAMPLE 24

To α-bromoisovaleric acid (1.2 g, 0.00603 mole) in methanol (2 ml) at 5°, is added dropwise methanolic sodium hydroxide to the phenolphthalein end point. The sodium salt of the acid is isolated under vacuum, and to the acid salt is added 2,6-dimethylaniline (3.65 g, 0.03015 mole) and the slurry heated in a pressure vessel at about 150° for 12 hours. Upon cooling, water (20 ml) is added to the reaction mixture and the excess 2,6-dimethylaniline extracted with ether (3×20 ml). The aqueous base layer is acidified with 2 N sulfuric acid to about pH 4 and the N-(2,6-dimethylphenyl)valine is extracted with ether (3×20 ml). The combined ether layers are washed with water (2×20 ml) until neutral and with brine (10 ml) followed by drying over calcium sulfate. The N-(2,6-dimethylphenyl)valine is isolated by concentration under vacuum.

To N-(2,6-dimethylphenyl)valine (1.07 g, 0.00486 mole) in THF:HMPT (3 ml:3 ml) at 24° is added m-phenoxybenzyl bromide (1.28 g, 0.00486 mole) and potassium carbonate (0.670 g, 0.00486 mole), and the slurry is stirred at 24° for 16 hours. The product is isolated by pouring the reaction mixture into ice-water (20 ml) and extracting with ether (3×20 ml). The combined ether extracts are washed with water (2×20 ml) and brine (10 ml) and dried over calcium sulfate. The product is concentrated under vacuum and purified by preparative TLC to give m-phenoxybenzyl ester of N-(2,6-dimethylphenyl)valine, MS m/e 403.2 (M+).

EXAMPLE 25

Following the procedure of Example 17 or 24, 3-fluoro-4-methylaniline is reacted with α-bromoisovaleric acid to prepare N-(3-fluoro-4-methylphenyl)valine, which is reacted with α-ethynyl-m-phenoxybenzyl bromide to yield the α-ethynyl-m-phenoxybenzyl ester of N-(3-fluoro-4-methylphenyl)valine, MS m/e 431 (M+).

N-(2-fluoro-4-methylphenyl)valine is prepared from α-bromoisovaleric acid and 2-fluoro-4-methylaniline and then reacted with α-ethynyl-m-phenoxybenzyl bromide to yield the α-ethynyl-m-phenoxybenzyl ester of N-(2-fluoro-4-methylphenyl)valine, MS m/e 431 (M+, 180).

EXAMPLE 26

To the m-phenoxybenzyl ester of N-(p-trifluoromethylphenyl)valine (1.57 g) in about 15 ml benzene, with stirring and under nitrogen, is added N-chlorosuccinimide (0.53 g). The reaction mixture is heated to reflux for about 2 hours. The reaction is cooled and partitioned between ether and water. Aqueous phase is back-extracted with ether. The combined ether phases are washed with water and brine, dried over sodium sulfate, filtered and evaporated. The reaction product is put on preparative TLC plates and eluted using 10% ether/hexane to yield the m-phenoxybenzyl ester of N-(2-chloro-4-trifluoromethylphenyl)valine, MS m/e 477.1 (M+).

Following the above procedure, there is prepared the m-phenoxy-α-cyanobenzyl ester of N-(2-chloro-4-trifluoromethylphenyl)valine, MS m/e 486.3 (M+), from the m-phenoxy-α-cyanobenzyl ester of N-(p-trifluoromethylphenyl)valine.

EXAMPLE 27

To N-phenylvaline hydrochloride (0.1 mole) in ether-THF at 5° is added dimethylformamide (0.06 mole) followed by dropwise addition of thionylchloride (0.15 mole). The reaction is stirred at 24° for 2.5 hours. The acid chloride hydrochloride is isolated and then in THF-ether, at 5°, is added α-cyano-3-phenoxybenzyl alcohol (0.09 mole) followed by slow addition of pyridine (0.3 mole). The reaction mixture is stirred at 24° for 17 hours and the product is worked up as in Example 6 to yield the 3-phenoxy-α-cyanobenzyl ester of N-phenylvaline.

EXAMPLE 28

Into a mixture of 1.0 g of the m-phenoxybenzyl ester of N-(p-methylphenyl)valine and 10 ml of ether, with stirring and cooled in an ice bath, is bubbled hydrogen chloride gas for about 15 minutes. The reaction product is filtered, washed with ether and recrystallized from hot ethanol to yield the hydrogen chloride salt of the m-phenoxybenzyl ester of N-(p-methylphenyl)valine, m.p. 151°-153°.

Following the procedure of Example 6, 2-fluoro-4-trifluoromethylaniline is reacted with α-cyano-m-phenoxybenzyl α-bromosiovalerate to yield the α-cyano-m-phenoxybenzyl ester of N-(2-fluoro-4-trifluoromethylphenyl)valine, MS m/e 502.1 (M+).

EXAMPLE 29

To a solution of 15.8 g (0.1 mole) ethyl 3,3-dimethyl-2-oxo-butyrate [Rabjohn et al., *J. Org. Chem.* 35, 3726 (1970)] is added 12.7 g (0.1 mole) p-chloroaniline and a catalytic amount (0.2 g) of p-toluenesulfonic acid. The solution is heated under reflux and water removed with a Dean-Stark trap. After 5 hours heating, the solution is poured into ether and this fraction is washed with saturated sodium bicarbonate and saturated brine solutions, and then dried over calcium sulfate. Removal of solvent by rotoevaporation yield the desire imine ester.

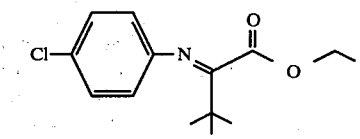

To a solution of 13.4 g (0.05 mole) imine ester in 100 ml methanol at 10° is added excess (2 g, 0.032 mole) sodium cyanoborohydride in portions. The pH of the solution is maintained at about pH 6 during the course of the reduction by adding concentrated sulfuric acid. After several hours, the reaction is stopped, most of the alcohol is removed by rotoevaporation, and the residue is poured into ether and water. The organic fraction is washed with saturated brine solution and dried over calcium sulfate. Removal of solvent by rotoevaporation gives ethyl 2-(p-chlorophenylamino)-3,3-dimethylbutyrate.

A solution of 2.7 g (0.01 mole) of the above ethyl amino ester and 0.4 g (0.01 mole) of sidum hydroxide in 17 ml ethanol and 3 ml water is stirred at toom temperature for 2 days. The alcohol and water are removed by rotoevaporation under high vacuum to give the sodium salt of 2-(p-chlorophenylamino)-3,3-dimethylbutyric acid. To the sodium salt is added 50 ml HMPT and 2.63 g (0.01 mole) of m-phenoxybenzyl bromide. After overnight stirring, the reaction is poured into water and ether-hexane (1:1). The organic phase is washed several times with water and then dried over calcium sulfate. Removal of solvent by rotoevaporation gives the 3-phenoxybenzyl ester of 2-(p-chlorophenylamino)-3,3-dimethylbutyric acid, MS m/e 423 (M+).

The process of this example is repeated using 0.1 mole of ethyl 3,3,3-trifluoro-2-oxo-propionate in place of ethyl 3,3-dimethyl-2-oxo-butyrate to give as the final product the 3-phenoxybenzyl ester of 2-(p-chlorophenylamino)-3,3,3-trifluoropropionic acid.

EXAMPLE 30

N-(4-chlorophenyl)valine is reacted with m-phenoxy-α-methylbenzyl bromide in THF/HMPT and potassium carbonate to yield the m-phenoxy-α-methylbenzyl ester of N-(4-chlorophenyl)valine, MS m/e 423 (M+). The m-phenoxy-α-methylbenzyl bromide is prepared from m-phenoxybenzaldehyde by reaction with methyllithium to the secondary alcohol which is brominated using phosphorous tribromide.

EXAMPLE 31

A mixture of 10 g of 4-fluoronitrobenzene, 5 g of valine and 10 g of sodium bicarbonate is dissolved in 200 ml of ethanol and 100 ml of water. The reaction mixture is refluxed for 3 hours and cooled. Excess 4-fluoronitrobenzene is removed by ether extraction and the aqueous phase is brought to pH 3 to 4 with hydrochloric acid. The oily precipitate is extracted with methylene chloride. After drying and removal of solvent, the residue is treated with 3 equivalents of sodium carbonate and 1 equivalent of m-phenoxybenzyl bromide in dimethylformamide as solvent. After stirring 24 hours the mixture is diluted with water and extracted with ether. The organic phase is washed with water, dried and the solvent removed. The crude ester is purified by preparative TLC to give the m-phenoxybenzyl ester of N-(p-nitrophenyl)valine.

EXAMPLE 32

To a solution of 1.51 g of N-phenylglycine in 10 ml of dry dimethylformamide is added 2.76 g of dry potassium carbonate and 1.04 g of 3,3-dimethyl-2-propenyl chloride. The mixture is stirred overnight at room temperature and then diluted with water and extracted with ether. The ether extracts are combined and washed with water, dried over magnesium sulfate and ether evaporated to give the 3,3-dimethyl-2-propenyl ester of N-phenylglycine.

To a solution of 2.19 g of the ester prepared above in 20 ml of THF and 5 ml of HMPT is added a solution of 1.03 g of lithium diisopropylamide in THF (prepared in situ from 1.01 g of diisopropylamine and 6.25 ml of 1.6 M butyl lithium) while maintaining temperature of about −60°. The reaction is allowed to reach −30°, then 1.08 g of trimethylsilyl chloride in 5 ml of THF is added at −30° and then stirred for 20 minutes. The reaction is then cooled to −78° and an additional 1.03 g of lithium diisopropylamide in THF added. The reaction is stirred at −60° for 30 min. and 1.08 g of trimethylsilyl chloride is added at −60°. After an hour at −60° the reaction is allowed to reach room temperature and 1 hour thereafter the reaction mixture is brought to reflux for 30 minutes. The reaction is cooled and poured into 10 ml of 2 N sodium hydroxide. The mixture is stirred for 20 minutes at room temperature and then extracted with ether. The aqueous phase is acidified to pH 3-4 and re-extracted with ether. The ether extracts are combined and washed with water, dried and evaporated to give 2-phenylamino-3,3-dimethyl-4-pentenoic acid which is esterified using m-phenoxybenzyl bromide by procedures hereinabove to yield m-phenoxybenzyl 2-phenylamino-3,3-dimethyl-4-pentenoate [m-phenoxybenzyl 2-phenylamino-2-(2-methyl-3-buten-2-yl)acetate].

EXAMPLE 33

A solution of 2 g of α-bromoisovaleric acid and 10 ml of methanol is titrated, at 0°, to the phenolphthalein end point with sodium hydroxide/methanol solution. The solvent is then removed, 6 ml of dimethylformamide and 2.97 g of p-acetylaniline added. The resulting clear reaction mixture is heated at 100° for 3 hours and then stirred overnight at room temperature. The reaction is poured into 50 ml of 0.1 N sodium hydroxide and washed with ether. The aqueous phase is acidified to pH 4 with concentrated hydrochloric acid and extracted 3× with chloroform. The chloroform extracts are dried and concentrated. The concentrate is taken up with 0.1 N sodium hydroxide and washed with ether. The aqueous phase is acidified and worked up as before to give 1.0 g of N-(p-acetylphenyl)valine which is reacted with 1.05 g of m-phenoxybenzyl bromide in dimethylformamide with potassium carbonate by procedures hereinabove to yield the m-phenoxybenzyl ester of N-(p-acetylphenyl)valine, MS m/e 417.1 (M+).

Following the above procedure, N-(p-cyanophenyl)valine is prepared from 0.011 mole of α-bromoisovaleric acid and 0.022 mole of p-cyanoaniline. Then 0.01 mole of N-(p-cyanophenyl)valine is esterified using 0.01 mole of m-phenoxybenzyl bromide and 0.020 mole of potassium carbonate in dimethylformamide to prepare the m-phenoxybenzyl ester of N-(p-cyanophenyl)valine, MS m/e 400.1 (M+).

EXAMPLE 34

The process of Example 29 is repeated using 0.1 mole of ethyl 3,3,3-trichloro-2-oxopropionate in place of ethyl 3,3-dimethyl-2-oxo-butyrate to give as the final product the 3-phenoxybenzyl ester of 2-(p-chlorophenylamino)-3,3,3-trichloropropionic acid.

EXAMPLE 35

A 100 ml flask is flushed with nitrogen and to it is added 25 ml of a 1 M THF solution of lithium N-isopropylcyclohexylamide (0.025 mole) followed by HMPT (5 ml). The flask is cooled to −78° and 7.1 g (0.025 mole) of m-phenoxybenzyl 3-methyl-2-butenoate in THF (25 ml) is added dropwise over 5 minutes. After the addition the mixture is stirred at −20° for 1 hour. This cold solution is then added dropwise to 1.1 equivalent of bromine in THF at −78°. After a further 1 hour at −78°, 5 ml of concentrated hydrochloric acid is added and the mixture allowed to come to RT and poured into ether plus cold aqueous hydrochloric acid. The ether layer is washed with water and brine and dried over calcium sulfate. Removal of the solvent gives m-phenoxybenzyl 2-bromo-3-methyl-3-butenoate, which is reacted with p-methylaniline by the process of Example 5 to give m-phenoxybenzyl ester of 2-(p-methylphenylamino)-3-methyl-3-butenoate.

EXAMPLE 36

Following the procedure of Example 1, the m-phenoxybenzyl ester of α-bromoisovaleric acid is reacted with 3,4-methylenedioxyaniline (3 equivalents) at about 75° for about 14 hours to yield the m-phenoxybenzyl ester of N-(3,4-methylenedioxyphenyl)valine, MS m/e 419 (M+, 13.2), 192 (100).

Following the above procedure, the m-phenoxybenzyl ester of N-(3-methoxyphenyl)valine, MS m/e 405 (M+, 4.1), 178 (100), is prepared from m-anisidine.

EXAMPLE 37

A mixture of N-chlorosuccinimide (1.17 mmole), m-phenoxybenzyl ester of N-(p-methoxyphenyl)valine (1.23 mmole) and benzene (20 ml) is refluxed under nitrogen for about 60 hours. The reaction is worked up in water/ether. The ether layer is washed with water and brine and dried over sodium sulfate. The crude product is purified by preparatory TLC eluting with 15% ether/hexane to give the m-phenoxybenzyl ester of N-(2-chloro-4-methoxyphenyl)valine, MS m/e 439 (M+, 7.4), 212 (100).

EXAMPLE 38

A solution of α-bromoisovaleric acid (8.17 mmole) in methanol is titrated to the phenophthalein end point using sodium methoxide. The solvent is removed by rotoevaporation and then there is added potassium carbonate (1.69 g), 2-fluoro-4-methylaniline (16.38 mmole) and 3 ml HMPT. The reaction is heated at 60° for about 5 hours and then worked up with 5% sodium hydroxide/ether and washed with water (3×). The basic layer is acidified and extracted with ether, washed with water and brine, dried over sodium sulfate and rotoevaporated to yield α-(2-fluoro-4-methylphenylamino)isovaleric acid. (2-Fluoro-4-methylaniline is prepared from 3-fluoro-4-nitrotoluene in a Parr bottle using platinum oxide and hydrogen in ethanol.)

To a mixture of 5.15 mmole of α-(2-fluoro-4-methylphenylamino)isovaleric acid, potassium carbonate (6.44 mmole), 4 ml of HMPT and 3 ml of THF, stirred, is added 5.13 mmole of m-phenoxybenzyl bromide. The reaction is stirred overnight at RT. The reaction is poured into 5% sodium hydroxide/ether, extracted with water (2×) and then washed with water (2×), dried over sodium sulfate and rotoevaporated under vacuum. The crude product is subjected to preparatory TLC eluting with 10% ether/hexane to give m-phenoxybenzyl ester of N-(2-fluoro-4-methylphenyl)valine.

NMR (CDCl$_3$) δ0.98 [d, 3, J−7 Hz, CH(CH$_3$)$_2$], 1.02 [d, 3, J=7 Hz, CH(CH$_3$)$_2$],

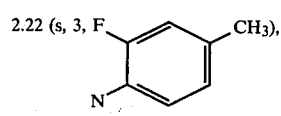

and 5.13 ppm (s, 2, ArCH$_2$O). IR (neat))1734 cm$^{-1}$ (C=O).

Following the above procedure, N-(4-tert-butylphenyl)valine is reacted with m-phenoxybenzyl bromide to yield the m-phenoxybenzyl ester of N-(4-tert-butylphenyl)valine.

NMR (CDCl$_3$) δ centered at 0.99 [d, 6, J=7 Hz, (CH$_3$)$_2$CH], 1.28 [s, 9, (CH$_3$)$_3$C-Ar], 3.93 (m, 2, NH and 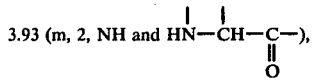), and 5.11 ppm (s, 2, ArCH$_2$O). IR (film) 1743 cm$^{-1}$ (C=O).

The procedure of this example is used to prepare N-(3-chloro-4-fluorophenyl)valine and N-(3-fluoro-4-methylphenyl)valine, each of which is reacted with m-phenoxybenzyl bromide to yield the m-phenoxybenzyl ester of N-(3-chloro-4-fluorophenyl)valine [MS m/e 427 (M+, 3.2), 200 (100)] and the m-phenoxybenzyl ester of N-(3-fluoro-4-methylphenyl)valine. NMR (CDCl$_3$) δ centered at 0.97 [d, 6, J=7 Hz, CH(CH$_3$)$_2$],

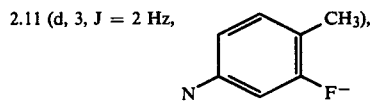

2.11 (d, 3, J = 2 Hz, and 5.10 ppm (s, 2, ArCH$_2$O). IR (neat 1732 cm$^{-1}$ (C=O).

EXAMPLE 39

A mixture of 5 g of p-trifluoromethylaniline, 2.25 g of α-bromoisovaleric acid and 2.0 g of potassium carbonate is heated at 100° for 1 hour. After 1.5 hour, 5 ml of HMPT is added and the mixture heated at 100° for 15 hr. The mixture is then poured into water and potassium carbonate added to about pH 11. The mixture is washed with ether, methylene chloride and the aqueous phase acidified to about pH 3 and washed with ether and concentrated. The residue is recrystallized from hexane/ether to yield N-(4-trifluoromethylphenyl)valine, which is reacted with m-phenoxybenzyl bromide to yield the m-phenoxybenzyl ester of N-(4-triflurormethylphenyl)valine. MS m/e 443 (M+, 5.9).

The acid, N-(4-trifluoromethylphenyl)valine, is reacted, at RT in DMF/THF and potassium carbonate, with m-phenoxy-α-ethynylbenzyl bromide to yield the m-phenoxy-α-ethynylbenzyl ester of N-(4-trifluoromethylphenyl)valine. MS m/e 467 (M+, 1.3), 216 (100).

The acid, N-(4-fluorophenyl)valine is prepared as above from 4-fluoroaniline and α-bromoisovaleric acid and then reacted with m-phenoxybenzyl bromide, as above, to yield the m-phenoxybenzyl ester of N-(4-fluorophenyl)valine.

NMR (CDCl$_3$) δ centered at 0.90 [m, 6, (CH$_3$)$_2$CH], 2.0 [m, 1, (CH$_3$)$_2$CH], 3.80 (m, 2, NH and 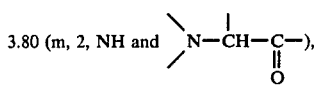), and 5.15 ppm (s, 2, ArCH$_2$O). IR (film) 3400 cm$^{-1}$ (NH).

N-(3-fluorophenyl)valine (prepared by reacting α-bromoisovaleric acid and 3-fluoroaniline at 140°, under nitrogen, for 3.5 hr) is reacted with m-phenoxybenzyl bromide in HMPT/THF and potassium carbonate at RT to yield the m-phenoxybenzyl ester of N-(3-fluorophenyl)valine. MS m/e 393 (M+, 2), 166 (100).

N-(2-chloro-4-methylphenyl)valine is prepared as above from α-bromoisovaleric acid and 2-chloro-4-methylaniline and then reacted with m-phenoxybenzyl bromide, as above, to yield the m-phenoxybenzyl ester of N-(2-chloro-4-methylphenyl)valine. MS m/e 423 (M+, 4), 196 (100).

Similarly, there is prepared the m-phenoxybenzyl ester of N-(3-nitrophenyl)valine from N-(3-nitrophenyl)valine and m-phenoxybenzyl bromide. MS m/e 420 (M+, 4), 193 (100).

EXAMPLE 40

To 1.21 mmole of triethyl oxonium tetrafluoroborate in about 5 ml methylene chloride under nitrogen is added 1.05 mmole of the m-phenoxybenzyl ester of N-(4-chlorophenyl)valine. The reaction is stirred at RT overnight and then poured into ether/water. The organic phase is washed with water and brine, dried over calcium sulfate, and solvent removed. The crude product is applied to preparatory TLC eluting with 20% ether/hexane, to give the m-phenoxybenzyl ester N-ethyl,N-(4-chlorophenyl)valine. MS m/e 437 (M+, 3), 210 (100).

EXAMPLE 41

N-(4-fluoro-2-methylphenyl)valine prepared from 4-fluoro-2-methylaniline and α-bromoisovaleric acid is reacted with m-phenoxybenzyl bromide as in Example 38 to give the m-phenoxybenzyl ester of N-(4-fluoro-2-methylphenyl)valine. MS m/e 407.2 (M+, 4.5), 180 (100).

EXAMPLE 42

To a mixture of 0.47 g of N-(4-methylphenyl)valine, 5 ml of HMPT, and 0.36 g of potassium carbonate, with stirring, is added 0.82 g of m-(3,4-dichlorophenoxy)benzyl bromide. The reaction mixture is stirred overnight at RT and then worked up by partition between water/ether. The aqueous phase is extracted with ether (2×) and then the combined ether phases are washed with water and brine, dried over sodium sulfate, filtered and evaporated. The concentrate is subjected to preparatory TLC eluting with 10% ether/hexane to yield the m-(3,4-dichlorophenoxy)benzyl ester of N-(4-methylphenyl)valine. MS m/e 459.1 (M+, 2.4), 162.1 (100).

The m-phenoxybenzyl ester of N-(2-nitrophenyl)valine, MS m/e 420.1 (M+, 2.7), 193 (100), is prepared from the reaction of m-phenoxybenzyl bromide and N-(2-nitrophenyl)valine as above.

N-(4-methylphenyl)valine is reacted with m-phenoxy-α-ethynylbenzyl bromide in DMF/THF and potassium carbonate at RT, as above, to give the m-phenoxy-α-ethynylbenzyl ester of of N-(4-methylphenyl)valine. MS m/e 413.1 (M+, 3.8), 162.1 (100).

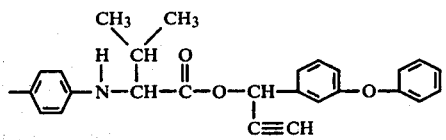

N-(3,4,5-trichlorophenyl)valine, prepared from 3,4,5-trichloroaniline and α-bromoisovaleric acid, is reacted with m-phenoxybenzyl bromide in HMPT/THF and potassium carbonate at RT to yield the m-phenoxybenzyl ester of N-(3,4,5-trichlorophenyl)valine. MS m/e 477.1 (M+, 9.8), 250 (100).

EXAMPLE 43

A mixture of 3,5-dimethoxyaniline (2.1 g), the m-phenoxybenzyl ester of α-bromoisovaleric acid (1.0 g), potassium iodide (72.9 mg) and 5 ml of HMPT is heated overnight at 70°–80°. The reaction is then worked up by partition between 100 ml of 2 N sulfuric acid and 100 ml of ether. The aqueous phase is extracted with ether and then the combined ether phases are washed with 2 N sulfuric acid, saturated sodium bicarbonate and brine, dried over potassium carbonate, filtered and evaporated. The residue is subjected to prep. TLC eluting with ether/hexane to yield the m-phenoxybenzyl ester of N-(3,5-dimethoxyphenyl)valine. MS m/e 435.2 (M+, 11.7), 208.1 (100).

By the above procedure, 3,4,5-trimethoxyaniline is reacted with m-phenoxybenzyl α-bromoisovalerate to yield the m-phenoxybenzyl ester of N-(3,4,5-trimethoxyphenyl)valine. MS m/e 465.2 (M+, 39.0), 182.9 (100).

Following the procedures of Example 42, N-(4-chlorophenyl)valine is reaction with m-benzylbenzyl bromide to yield the m-benzylbenzyl ester of N-(4-chlorophenyl)valine. MS m/e 407.1 (M+, 6.2), 182 (100).

EXAMPLE 44

To m-phenoxybenzyl 3-methyl-2-butenoate (5.80 mmole) and carbon tetrachloride (30 ml), under nitrogen, is slowly added bromine (5.99 mmole) in carbon tetrachloride with the reaction flask in an ice-bath. After about 3 hr, the reaction is worked up by partition between water/ether. The aqueous phase is extracted with ether and then the combined ether phases are washed with water and brine, dried over potassium carbonate, filtered and evaporated to yield m-phenoxybenzyl 2,3-dibromo-3-methylbutanoate.

A mixture of the above dibromo ester (4.1 mmole), 4-methylaniline (12.6 mmole), triethylamine (8.6 mmole), THF (20 ml) and HMPT (2 ml) is heated at 50° under nitrogen. After 9 days, the reaction is worked up by partition between ether/2 N HCl. The aqueous phase is extracted with ether and then the combined ether phases are washed with 2 N HCl and brine, dried over potassium carbonate, filtered and evaporated. The residue is subjected to prep. TLC eluting with 10% ether/hexane to yield the m-phenoxybenzyl ester of α-(4-methylphenylamino)-3-methyl-3-butenoic acid. MS m/e 387.2 (M+, 2.7), 160 (100).

EXAMPLE 45

To N-(4-chlorophenyl)isoleucine (0.57 g) in about 5 ml of HMPT is added potassium carbonate (0.54 g) and then m-phenoxybenzyl bromide (1.09 g). The reaction mixture is stirred overnight at RT. The reaction is worked up by partition between water/ether. The aqueous phase is extracted with ether and then the combined ether phases are washed with water and brine, dried over potassium carbonate, filtered and evaporated. The residue is subjected to prep. TLC eluting with 10% ether/hexane to yield the m-phenoxybenzyl ester of N-(4-chlorophenyl)isoleucine. MS m/e 423 (M+, 3.7), 196 (100).

N-(4-chlorophenyl)isoleucine is prepared by the reaction of 4-chloroaniline with the sodium salt of α-bromo-3-methylpentanoic acid neat at 100°.

By the above procedure, m-phenoxybenzyl bromide is reacted with N-(4-methylphenyl)isoleucine to prepare the m-phenoxybenzyl ester of N-(4-methylphenyl)isoleucine. MS m/e 403.3 (M+, 3.3), 176.1 (100).

EXAMPLE 46

N-(4-methylphenyl)valine is reacted with m-(4-methoxyphenoxy)benzyl bromide in THF/HMPT and potassium carbonate at RT overnight to yield the m-(4-methoxyphenoxy)benzyl ester of N-(4-methylphenyl)-valine. IR (film) 3380 cm$^{-1}$ (NH) and 1735 cm$^{-1}$ (C=O).

EXAMPLE 47

To the m-phenoxybenzyl ester of N-(4-chlorophenyl)valine (1.19 mmole) in ether (4.5 ml), under nitrogen, is added dimethylaminopyridine (4.25 mmole) which is cooled in an ice-bath and then trichloroacetyl chloride (3.58 mmole) in ether added slowly. The reaction mixture is heated at 40° for 3 days. The reaction is worked up with ether/water. The aqueous phase is extracted with ether and then the combined ether phases are washed with water and brine and dried over sodium sulfate. The residue is subjected to prep. TLC eluting with 10% ether/hexane to yield the m-phenoxybenzyl ester of N-trichloroacetyl,N-(4-chlorophenyl)-valine. MS m/e 553 (M+, 1.8), 183 (100).

EXAMPLE 48

Following the procedure of Example 47, the m-phenoxybenzyl ester of N-acetylformyl,N-(4-chlorophenyl)valine [MS m/e 479 (M+, 0.5), 183 (100)] is prepared by the reaction of the acid chloride of pyruvic acid with the m-phenoxybenzyl ester of N-(4-chlorophenyl)valine.

EXAMPLE 49

Following the procedure of Example 42, N-(4-chlorophenyl)valine is reacted with m-(3,4-dichlorophenoxy)benzyl bromide to yield the m-(3,4-dichlorophenoxy)benzyl ester of N-(4-chlorophenyl)valine. MS m/e 477 (M+, 2.1), 182 (100).

EXAMPLE 50

To the m-phenoxybenzyl ester of N-(4-methoxyphenyl)valine (0.89 mmol) in ether is added trifluoroacetic anhydride (4.46 mmol), under nitrogen. The reaction mixture is stirred for 2.5 hr and then worked up with ether/water. The combined ether layers are washed with saturated sodium bicarbonate and brine, dried over sodium sulfate and evaporated to yield the m-phenoxybenzyl ester of N-trifluoroacetyl,N-(4-methoxyphenyl)valine. MS m/e 501 (M+, 22.5), 183 (100).

EXAMPLE 51

A mixture of the m-phenoxybenzyl ester of N-(4-chlorophenyl)valine (1.22 mmole), acetic formic anhydride in acetic acid (23.8 mmole, 2.1 g) and formic acid (1.5 ml) is stirred overnight at RT under nitrogen. The reaction product is concentrated and then subjected to prep. TLC eluting with 20% ethylacetate/hexane to yield the m-phenoxybenzyl ester of N-formyl,N-(4-chlorophenyl)valine, MS m/e 437 (M+, 8.1), 182 (100).

EXAMPLE 52

Following the procedure of Example 50, trifluoroacetate anhydride and the m-phenoxybenzyl ester of N-(4-chlorophenyl)valine are reacted to yield the m- phenoxybenzyl ester of N-trifluoroacetyl,N-(4-chlorophenyl)valine, MS m/e 505 (M+, 14.9), 278 (100).

Following the procedure of, for example, Example 42, α-ethynyl-m-phenoxybenzyl bromide and N-(4-chlorophenyl)valine are reacted to yield the α-ethynyl-m-phenoxybenzyl ester of N-(4-chlorophenyl)valine, MS m/e 433 (M+, 2.2), 182 (100).

EXAMPLE 53

To the m-phenoxybenzyl ester of N-phenyl valine (1.2 mmole) is added 12.5% phosgene in benzene (2.3 mmole), cooled in an ice bath, and then dimethylaminopyridine (1.22 mmole). The reaction mixture is stirred at RT for 3 days. Then one ml of benzene, 0.15 g of dimethylaminopyridine and 2 ml of phosgene are added and the reaction stirred overnight at RT. The reaction is worked up using chloroform/water. The chloroform layer is washed with dilute sulfuric acid, water and brine, dried over sodium sulfate and filtered. The solvent is removed by rotoevaporation to yield the m-phenoxybenzyl ester of N-chloroformyl,N-phenyl valine.

A mixture of 0.89 mmole of the foregoing ester, one ml of pyridine and methanol (0.91 mmole) is stirred at RT for 4 days. The reaction is then worked up using dilute HCl/ether. The ether layer is washed with aqueous HCl, water and brine, dried over sodium sulfate and filtered. Solvent is removed and residue plated on prep. TLC plate eluting with 8%, 20% ether-hexane to yield the m-phenoxybenzyl ester of N-methoxycarbonyl,N-phenyl valine, MS m/e 433 (M+, 6.7), 206 (100).

EXAMPLE 54

N-(2-chloro-4-cyanophenyl)valine and m-phenoxybenzyl bromide in THF/HMPT with potassium carbonate are reacted using the procedure of Example 42 to prepare the m-phenoxybenzyl ester of N-(2-chloro-4-cyanophenyl)valine, MS m/e 434 (M+, 3.7), 207 (100). N-(2-chloro-4-cyanophenyl)valine is prepared by the reaction of 2-chloro-4-cyanoaniline with α-bromoisovaleric acid using the process of, for example, Example 18.

Similarly, there is prepared N-(2,4-difluorophenyl)valine from 2,4-difluoroaniline and α-bromoisovaleric acid. The N-(2,4-difluorophenyl)valine is esterified using m-phenoxybenzyl bromide to prepare the m-phenoxybenzyl ester of N-(2,4-difluorophenyl)valine, MS m/e 411 (M+, 3.5), 184 (100).

EXAMPLE 55

N-(2-fluoro-4-chlorophenyl)valine and m-phenoxybenzyl bromide are reacted using the process of Example 42 to yield the m-phenoxybenzyl ester of N-(2-fluoro-4-chlorophenyl)valine, MS m/e 427.1 (M+, 4.1), 200 (100). N-(2-fluoro-4-chlorophenyl)valine is prepared by heating the potassium salt of α-bromoisovaleric acid and 2-fluoro-4-chloroaniline neat at 130° for about 2 hours.

Similarly, there is prepared N-(3-methyl-4-fluorophenyl)valine which is esterified using m-phenoxybenzyl bromide to yield the m-phenoxybenzyl ester of N-(3-methyl-4-fluorophenyl)valine, MS m/e 407.3 (M+, 0.3), 180 (100).

In the same way, there is prepared N-(3-methyl-6-fluorophenyl)valine and N-(3-fluoro-6-methylphenyl)valine, each of which is esterified using m-phenoxybenzyl bromide to yield the m-phenoxybenzyl ester of N-(3-methyl-6-fluorophenyl)valine [MS m/e 407.3 (M+, 4.3), 180 (100)] and the m-phenoxybenzyl ester of N-(3-fluoro-6-methylphenyl)valine [MS m/e 407.3 (M+, 3.9), 180 (100)].

EXAMPLE 56

To a mixture of the α-cyano-m-phenoxybenzyl ester of N-(4-chlorophenyl)valine (0.79 g) and about 20 ml of dry DMF is added about one ml of triethanolamine at RT. Into the mixture is slowly bubbled H₂S gas for about 3 hours. The reaction is then stirred overnight. The reaction is worked up by partition with ether/water. The organic phase is washed with brine (3×), dried over sodium sulfate, filtered and evaporated. The residue is plated on a prep. TLC plate eluting with 20% ethyl acetate/hexane to yield the desired thioamide, MS m/e 181.9 (100), IR (film) 3180 cm$^{-1}$ (NH) and 1740 cm$^{-1}$ (C=O).

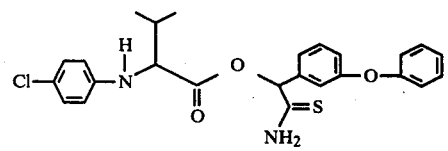

EXAMPLE 57

N-(2-cyano-4-chlorophenyl)valine is reacted with m-phenoxybenzyl bromide to yield the m-phenoxybenzyl ester of N-(2-cyano-4-chlorophenyl)valine using the procedure of Example 42. MS m/e 434.1 (M+, 3.5).

Similarly, there is prepared the α-cyano-m-phenoxybenzyl ester of N-(2-methylphenyl)valine, MS m/e 414.1 (M+, 5.8), from α-cyano-m-phenoxybenzyl bromide and N-(2-methylphenyl)valine.

Likewise, there is prepared the m-phenoxybenzyl ester of N-(2-methyl-4-chlorophenyl)valine, MS m/e 423.1 (M+, 16.9), from m-phenoxybenzyl bromide and N-(2-methyl-4-chlorophenyl)valine.

In the same way, N-(pentafluorophenyl)valine is reacted with m-phenoxybenzyl bromide to yield the m-phenoxybenzyl ester of N-(pentafluorophenyl)valine, MS m/e 465 (M+, 4.2).

EXAMPLE 58 m-Phenoxybenzyl bromide is reacted with each of N-(2,4-dimethoxyphenyl)valine and N-(2-methyl-6-chlorophenyl)valine following the procedure of Example 42 to yield the m-phenoxybenzyl ester of N-(2,4-dimethoxyphenyl)valine, MS m/e 435.2 (M+, 12.4), and the m-phenoxybenzyl ester of N-(2-methyl-6-chlorophenyl)valine, MS m/e 423.1 (M+, 3.7).

EXAMPLE 59

A mixture of 0.5 g of the m-phenoxybenzyl ester of N-(2,6-dimethylphenyl)valine, 0.21 g of N-chlorosuccinimide and 3 ml of benzene is heated at reflux for 2 hours. The reaction is diluted with hexane, washed with water (2×) and solvent stripped to give the crude product. To the crude product is added 0.1 g of N-chlorosuccinimide and 3 ml benzene. The mixture is heated at reflux for 30 min and then allowed to stand overnight at RT. The reaction is worked up by diluting with hexane, washing with water and stripping off solvent to yield the m-phenoxybenzyl ester of N-(2,6-dimethyl-4-chlorophenyl)valine, MS m/e 437.1 (M+, 15.3).

EXAMPLE 60

N-(4-bromophenyl)valine, prepared from 4-bromoaniline and α-bromoisovaleric acid, is esterified using m-phenoxybenzyl bromide to yield the m-phenoxybenzyl ester of N-(4-bromophenyl)valine, MS m/e 454 (M+).

The sodium salt of α-bromoisovaleric acid is reacted with p-ethylaminobenzoate, neat, at 140° for 3 hr to yield N-(4-ethoxycarbonylphenyl)valine, which is reacted with m-phenoxybenzyl bromide to yield the m-phenoxybenzyl ester of N-(4-ethoxycarbonylphenyl))valine, MS m/e 447 (M+).

The m-phenoxybenzyl ester of N-(3-trifluoromethylphenyl)valine, MS m/e 443 (M+), is prepared from N-(3-trifluoromethylphenyl)valine and m-phenoxybenzyl bromide. The reaction of 3-trifluoromethylaniline with the sodium salt of α-bromoisovaleric acid provides the starting material.

Each of N-(3,4-dimethylphenyl)valine, N-(3-methylphenyl)valine, N-(2,4,6-trimethylphenyl)valine, N-(2-chloro-5-trifluoromethylphenyl)valine and N-(2,6-difluoro-4-chlorophenyl)valine is esterified using m-phenoxybenzyl bromide with potassium carbonate in THF/HMPT at RT to yield the respective ester below.

The m-phenoxybenzyl ester of
N-(3,4-dimethylphenyl)valine, MS m/e 403.2 (M+),
N-(3-methylphenyl)valine, MS m/e 389.2 (M+),
N-(2,4,6-trimethylphenyl)valine, MS m/e 417.1 (M+),
N-(2-chloro-5-trifluoromethylphenyl)valine, MS m/e 477 (M+), and
N-(2,6-difluoro-4-chlorophenyl)valine, MS m/e 445.1 (M+).

The starting material is prepared by the reaction of the sodium salt of α-bromoisovaleric acid with each of 3,4-dimethylaniline, 3-methylaniline, 2,4,6-trimethylaniline, 3-chloro-5-trifluoromethylaniline and 2,6-difluoro-4-chloroaniline according to the procedure of Example 18.

Following the procedure of Example 1, each of 4-n-butylaniline and 4-cyclopropylaniline is reacted with m-phenoxybenzyl α-bromoisovalerate to yield the m-phenoxybenzyl ester of N-(4-n-butylphenyl)valine, MS m/e 431.2 (M+), and the m-phenoxybenzyl ester of N-(4-cyclopropylphenyl)valine, MS m/e 415.1 (M+).

Each of the m-phenoxybenzyl ester of N-(4-chlorophenyl)valine and N-(4-methylphenyl)valine is methylated using the procedure of Example 2 to yield the m-phenoxybenzyl ester of N-methyl, N-(4-chlorophenyl)valine, MS m/e 423 (M+), and the m-phenoxybenzyl ester of N-methyl, N-(4-methylphenyl)valine, MS m/e 403.2 (M+).

EXAMPLE 61

To a mixture of 10 g of ethyl crotonate, 40 ml of dioxane and 60 ml of water, at 0°, is slowly added 15 g of N-bromosuccinimide. After addition is complete, the reaction is allowed to stand at RT for 17 hr with stirring. The reaction is taken up in ether, washed with water and saturated sodium sulfite, dried over magnesium sulfate and evaporated under reduced pressure to yield ethyl 2-bromo-3-hydroxybutanoate.

To a mixture of ethyl 2-bromo-3-hydroxybutanoate (10 g) and 15 ml of HMPT is added 13.2 g of aniline. The reaction is stirred at RT for 3 days and then taken up in ether followed by washing with dilute sulfuric acid, pH 3, and water. The ether phase is dried over magnesium sulfate and evaporated to yield ethyl 2-phenylamino-3-hydroxybutanoate, which is saponified using 1.6 g of sodium hydroxide, 40 ml of methanol and 20 ml of water with stirring overnight at RT. The acid 2-phenylamino-3-hydroxybutanoic acid (3.0 g) is reacted with m-phenoxybenzyl bromide (3.4 g) in HMPT (20 ml) and potassium carbonate (2.12 g) at 35° for a few hours and worked up using ether/water to yield the m-phenoxybenzyl ester of 2-phenylamino-3-hydroxybutanoic acid.

To a solution of N-chlorosuccinimide (1.24 g) and dry THF (60 ml), stirring at RT, is slowly added triphenylphosphine (2.43 g) in 50 ml of THF. Then th m-phenoxybenzyl ester of 2-phenylamino-3-hydroxybutanoate (3.5 g) in 30 ml of THF is added slowly. The reaction mixture is stirred overnight. The reaction is then concentrated under reduced pressure. The residue (oil) is taken up in ether, washed with water, dried over magnesium sulfate and evaporated to yield the m-phenoxybenzyl ester of 2-phenylamino-3-chlorobutanoic acid, MS m/e 395 (M+).

The above prepared ester is methylated using the procedure of Example 2 to yield m-phenoxybenzyl 2-(methyl,phenylamino)-3-chlorobutanoate, MS m/e 409 (M+).

EXAMPLE 62

A mixture of 0.5 g of m-phenoxybenzyl 2-oxo-3-methylbutanoate, 0.39 g of 2,4,6-trichloroaniline, 0.02 g of p-toluenesulfanylacetate and 10 ml of benzene is heated to reflux for about 5.5 hr. A Dean-Stark trap is used to remove water. The reaction is worked by pouring into ether/sodium bicarbonate solution. The organic phase is washed with water and brine, dried over magnesium sulfate and evaporated. To the reaction product (0.79 g) is added 3 ml of methanol, 1 ml of THF and 0.19 g of NaCNBH$_3$. The reaction mixture is stirred at RT and then adjusted to pH 3 to 4 with concentrated sulfuric acid. Stirring at RT is continued overnight. The reaction is worked up as before using ether/sodium bicarbonate solution and subjected to prep. TLC eluting with 20% ether/hexane to yield the m-phenoxybenzyl ester of N-(2,4,6-trichlorophenyl)valine, MS m/e 477 (M+).

N-(2,4-dichlorophenyl)valine, prepared from 2,4-dichloroaniline and sodium salt of α-bromoisovaleric acid, is reacted with m-phenoxybenzyl bromide to yield the m-phenoxybenzyl ester of N-(2,4-dichlorophenyl)-valine, MS m/e 443 (M+).

Following the procedure of Example 6, α-cyano-m-phenoxybenzyl α-bromoisovalerate is reacted with each of 4-chloroaniline, 4-methoxyaniline and 4-methylaniline to prepare the α-cyano-m-phenoxybenzyl ester of
N-(4-chlorophenyl)valine, MS m/e 434.1 (M+),
N-(4-methoxyphenyl)valine, MS m/e 430.1 (M+), and
N-(4-methylphenyl)valine, MS m/e 414.2 (M+).

The α-cyano-m-phenoxybenzyl ester of N-(4-chlorophenyl)valine is reacted with methyl iodide using the procedure of Example 2 to yield the α-cyano-m-phenoxybenzyl ester of N-methyl,N-(4-chlorophenyl)-valine, MS m/e 448.1 (M+).

N-(2,3-dichlorophenyl)valine, prepared from 2,3-dichloroaniline and sodium salt of α-bromoisovaleric acid, is reacted with m-phenoxybenzyl bromide to yield the m-phenoxybenzyl ester of N-(2,3-dichlorophenyl)-valine, MS m/e 443 (M+).

EXAMPLE 63

Following the procedure of Example 1, m-phenoxybenzyl α-bromoisovalerate is reacted with each of 4-ethylaniline and 4-isopropylaniline to yield the m-phenoxybenzyl ester of N-(4-ethylphenyl)valine, MS m/e 403.2 (M+), and N-(4-isopropylphenyl)valine, MS m/e 417.2 (M+).

Following the procedure of Example 18, m-phenoxybenzyl bromide is reacted with each of N-(4-nitrophenyl)valine and N-(2,6-dichlorophenyl)valine to yield the respective m-phenoxybenzyl ester of N-(4-nitrophenyl)valine, MS m/e 420.1 (M+), and N-(2,6-dichlorophenyl)valine, MS m/e 443 (M+).

EXAMPLE 64

Following the procedure of Example 1, m-phenoxybenzyl α-bromoisovalerate is reacted with 3-chloroaniline to yield the m-phenoxybenzyl ester of N-(3-chlorophenyl)valine, MS m/e 409.2 (M+).

Following the procedure of Example 18, m-phenoxybenzyl bromide is reacted with each of N-(3-trifluoromethyl-4-chlorophenyl)valine, N-(2-chlorophenyl)valine, and N-(2,6-difluorophenyl)valine to yield the respective ester—the m-phenoxybenzyl ester of
N-(3-trifluoromethyl-4-chlorophenyl)valine, MS m/e 477.1 (M+),
N-(2-chlorophenyl)valine, MS m/e 409 (M+), and
N-(2,6-difluorophenyl)valine, MS m/e 411.1 (M+).

N-(4-t-butylphenyl)valine is reacted with benzyl bromide using the procedure of Example 18 to yield the benzyl ester of N-(4-t-butylphenyl)valine, MS m/e 431 (M+).

Following the procedure of Example 24, N-(4-chlorophenyl)valine is esterified using each of 4-allylbenzyl bromide, m-(3-trifluoromethylphenoxy)benzyl bromide, m-(4-chlorophenoxy)benzyl bromide, m-(4-methylphenoxy)benzyl bromide, m-(4-methoxyphenoxy)benzyl bromide, and m-(4-t-butylphenoxy)benzyl bromide to yield the respective esters—the 4-allylbenzyl ester of N-(4-chlorophenyl)valine, MS m/e 357.1 (M+); the m-(3-trifluoromethylphenoxy)benzyl ester of N-(4-chlorophenyl)valine, MS m/e 477 (M+); the m-(4-chlorophenoxy)benzyl ester of N-(4-chlorophenyl)valine, MS m/e 443 (M+); the m-(4-methylphenoxy)benzyl ester of N-(4-chlorophenyl)valine, MS m/e 423 (M+); the m-(4-methoxyphenoxy)benzyl ester of N-(4-chlorophenyl)valine, MS m/e 439 (M+); and the m-(4-t-butylphenoxy)benzyl ester of N-(4-chlorophenyl)valine, MS m/e 465.2 (M+).

Following the procedure of Example 42, N-(4-methylphenyl)valine is reacted with each of 4-allylbenzyl bromide, m-(3-trifluoromethyphenoxy)benzyl bromide, m-(4-methylphenoxy)benzyl bromide, m-(4-chlorophenoxy)benzyl bromide and m-(4-t-butylphenoxy)benzyl bromide to yield the respective esters—the 4-allylbenzyl ester of N-(4-methylphenyl)valine, MS m/e 337.1 (M+); the m-(3-trifluoromethylphenoxy)benzyl ester of N-(4-methylphenyl)valine, MS m/e 457.1 (M+); the m-(4-methylphenoxy)benzyl ester of N-(4-methylphenyl)valine, MS m/e 403.2 (M+); the m-(4-chlorophenoxy)benzyl ester of N-(4-methylphenyl)valine, MS m/e 423 (M+); and the m-(4-t-butylphenoxy)benzyl ester of N-(4-methylphenyl)valine, MS m/e 445.2 (M+).

EXAMPLE 65

To a mixture of N-(4-methylphenyl)valine (2.77 mmol), potassium carbonate (3.25 mmol) and HMPT (3 ml), with stirring and under nitrogen, at RT, is added 5-benzyl-3-furylmethyl bromide (2.77 mmol) in THF. The reaction is stirred at RT for about 48 hr and then worked up by partition between water/ether. The organic phase is washed with water and brine, dried over potassium carbonate, filtered and evaporated. The residue is plated on prep. TLC plate eluting with 10% ether/hexane to yield the 5-benzyl-3-furylmethyl ester of N-(4-methylphenyl)valine, MS m/e 377.1 (M+).

Following the procedure of Example 17, N-(2-trifluoromethylphenyl)valine, prepared from 2-trifluoromethylaniline and sodium salt of α-bromoisovaleric acid by the procedure of Example 18, is reacted with m-phenoxybenzyl bromide to yield the m-phenozybenzyl ester of N-(2-trifluoromethylphenyl)valine, MS m/e 443 (M+).

Using the procedure of Example 1, each of 2-methoxyaniline and 4-ethoxyaniline is reacted with m-phenoxybenzyl α-bromoisovalerate to yield the m-phenoxybenzyl ester of N-(2-methoxyphenyl)valine, MS m/e 405.2 (M+), and the m-phenoxybenzyl ester of N-(4-ethoxyphenyl)valine, MS m/e 419.1 (M+).

Following the procedure of Example 42, N-(3,4-dichlorophenyl)valine is reacted with m-phenoxybenzyl bromide to yield the m-phenoxybenzyl ester of N-(3,4-dichlorophenyl)valine, MS m/e 443 (M+).

Each of N-(3-cyanophenyl)valine and N-(3,4-dimethoxyphenyl)valine is reacted with m-phenoxybenzyl bromide using the procedure of Example 17 to yield the m-phenoxybenzyl ester of N-(3-cyanophenyl)valine, MS m/e 400.1 (M+), and the m-phenoxybenzyl ester of N-(3,4-dimethoxyphenyl)valine, MS m/e 435 (M+).

Following the procedure of Example 6, 4-trifluoromethylaniline is reacted with α-cyano-m-phenoxybenzyl α-bromoisovalerate to yield the α-cyano-m-phenoxybenzyl ester of N-(4-trifluoromethylphenyl)valine, MS m/e 468.2 (M+).

EXAMPLE 66

To p-nitrothiophenol (14.1 g) suspended in water (100 ml) at RT is added 2 N sodium hydroxide (52 ml). The mixture is stirred for 15 min and methyl iodide (9.4 ml) added slowly at 10°. The reaction mixture is warmed to RT and stirred for 2 hr. The reaction is worked up by extracting into ether (3×80 ml), washing with water and brine, drying over calcium sulfate and evaporating to give p-nitrophenyl methylsulfide (12.2 g).

To p-nitrophenyl methylsulfide (10.5 g) in chloroform (120 ml), cooled to 10°–17°, under nitrogen, is bubbled chlorine while illuminating with a lamp (150 watt). A trace of 2,2'-azobis-(2-methylpropionitrile) is added. After about 3 hr of passing chlorine through the solution, the reaction is terminated and nitrogen passed through for 0.5 hr. The solution is concentrated and the product, p-nitrophenyl trichloromethyl sulfide recrystallized out of hot acetone, m.p. 94°–96°.

p-Nitrophenyl trichloromethylsulfide (1.5 g) and purified SbF$_3$ (1.96 g) is stirred under nitrogen in a Claisen flask and heated to 110°–120°. After about 0.5 hr, the product is distilled off at 85°–90° (5 mm). The distillate is taken up in ether (50 ml) and the ether layer washed with 10% HCl until cloudiness no longer occurs on addition of water. The ether layer is washed with water until neutral and with brine, dried over calcium sulfate and evaporated to yield p-nitrophenyl trifluoromethyl sulfide.

To p-nitrophenyl trifluoromethyl sulfide (3.0 g) in absolute ethanol (30 ml) is added Adams catalyst ($Pt_2O$, 0.026 g). The mixture is hydrogenated in a Parr vessel at 50 lbs/sq. in. for about 15 min. The reaction is worked up by filtering through Celite and evaporating to yield p-aminophenyl trifluoromethyl sulfide.

Following the procedure of Example 43, p-aminophenyl trifluoromethyl sulfide is reacted with m-phenoxybenzyl α-bromoisovalerate to yield the m-phenoxybenzyl ester of N-(4-trifluoromethylthiophenyl)valine, MS m/e 475 ($M^+$).

Alternatively, using the procedure of Example 38, p-aminophenyl trifluoromethyl sulfide is reacted with the sodium salt of α-bromoisovaleric acid to yield N-(4-trifluoromethylthiophenyl)valine, which is esterified to yield the m-phenoxybenzyl ester of N-(4-trifluoromethylthiophenyl)valine.

EXAMPLE 67

To a a 100 ml, 3-necked flask equipped with addition funnel and reflux condensor to which is attached a water-gas trap, are placed 10.08 g (65 mmole) of 2-fluoro,4-nitrotoluene. The addition funnel is charged with 7.0 ml (22.3 g; 138 mmole) of bromine and the flask is heated. When the temperature (oil bath) is approximately 100°, the bromine is introduced slowly while illuminating the flask with a 150 watt light bulb. The bromination starts readily as the temperature is increased to approx. 160°-170° and HBr is smoothly evolved. After 4 hr, heating is discontinued. The cooled mixture is worked up by pouring into ice and saturated sodium bisulfite and extracting with ether (3×). The combined organic layers are washed once more with saturated $NaHSO_3$, brine (1×), and dried over sodium sulfate. Filtration and evaporation of the solvent yields 17.0 g of a mixture of the benzal bromide and benzyl bromide (1.7:1 by nmr analysis). The crude material is suspended in a hypobromite solution prepared by combining 60 g of sodium hydroxide and 20 ml of bromine in 600 ml of water. This mixture is stirred for 6 days at RT and then filtered to yield 2-fluoro,4-nitro-α,α,α-tribromotoluene, which may be recrystallized from methanol.

A mixture of 8.5 g of 2-fluoro,4-nitro-α,α,α-tribromotoluene (22 mmole) and 4.7 g (26 mmole) of antimony trifluoride are placed in a small flask equipped with a condenser set for distillation. The flask is heated slowly and the mixture distilled both at atmospheric pressure and then under reduced pressure until no further material distills. The distillate is partitioned between 6 N hydochloride acid and ether. The organic layer is then washed with 6 N sodium hydroxide (1×) and brine (1×) and dried over sodium sulfate. Filtration and evaporation of the solvent yielded 2-fluoro,4-nitrobenzotrifluoride.

To a solution of 20 ml of concentrated hydrochloric acid and 15 ml of 95% ethanol is added 5.0 g (24 mmole) of 2-fluoro,4-nitrobenzotrifluoride. The mixture is stirred and 20 g (88 mmole) of stannous chloride dihydrate is added in portions over a 30 min period. The reaction is exothermic and during the addition the temperature is maintained at 60°. When the addition is complete, the mixture is stirred at 60° for an additional 30 min. The reaction is cooled and poured onto a mixture of ice and 36% sodium hydroxide, which is extracted with ether (3×). The combined ether layers are washed once with brine and dried over sodium sulfate. Filtration and evaporation of the solvent gave 4-amino,2-fluorobenzotrifluoride (3-fluoro-4-trifluoromethylaniline).

Following the procedure of Example 38, 3-fluoro-4-trifluoromethylaniline is reacted with the sodium salt of α-bromoisovaleric acid to yield N-(3-fluoro-4-trifluoromethylphenyl)valine, which is esterified to yield the m-phenoxybenzyl ester of N-(3-fluoro-4-trifluoromethylphenyl)valine.

N-(2,4-dinitrophenyl)valine is reacted with m-phenoxybenzyl bromide using the procedure of Example 38 to yield the m-phenoxybenzyl ester of N-(2,4-dinitrophenyl)valine.

This procedure is repeated using 3-fluoro-4-nitrotoluene in place of 2-fluoro-4-nitrotoluene to prepare 2-fluoro-4-trifluoromethylaniline, which is converted into N-(2-fluoro-4-trifluoromethylphenyl)valine and then esterified to yield the m-phenoxybenzyl ester of N-(2-fluoro-4-trifluoromethylphenyl)valine, MS m/e 461.1 ($M^+$).

EXAMPLE 68

A mixture of 2-fluoro-4-chlorotoluene (25.05 g), $KMnO_4$ (55.04 g) and water (400 ml) is heated to reflux for about 5 hr. The reaction is then worked up by filtering while hot through Celite and the filtrate is acidified with 2 N HCl. White crystals are filtered off, dissolved in ether and washed with water and brine, dried over sodium sulfate, filtered and evaporated to yield 2-fluoro-4-chlorobenzoic acid.

A mixture of 2-fluoro-4-chlorobenzoic acid (6.05 g), polyphosphoric acid (62.51 g) and $CH_3NO_2$ (5.1 g) is heated at 130°. After about 2.5 hr, the reaction mixture is poured onto ice and made basic by addition of dilute sodium hydroxide. The reaction is then worked up by extracting with ether. The combined ether extracts are washed with water and brine, dried over sodium sulfate, filtered and evaporated to yield 2-fluoro-4-chloroaniline.

EXAMPLE 69

A mixture of N-(4-chlorophenyl)valine (0.6 g), m-phenoxybenzyl sulfide (0.57 g) and tetra(t-butoxy)titanate (0.9 g), in a flask fitted with a short path distillation head under nitrogen, is heated to about 150°, with stirring for about 7 hr, under vacuum (about 50 mm). The reaction mixture is allowed to cool and let stand for several hours. The reaction is worked up by adding ether and 2 N sulfuric acid, which is extracted with ether. The combined ether layers are washed with water, 10% sodium bicarbonate, water, brine, dried over calcium sulfate and rotoevaporated. The concentrate is placed on prep. TLC, eluting with 10% ether/hexane, and the main band collected to yield the m-phenoxybenzyl thiolester of N-(4-chlorophenyl)valine, m.p. 103.5°-105°.

The above process is repeated using N-(4-methylphenyl)valine to yield the m-phenoxybenzyl thiolester of N-(4-methylphenyl)valine, MS m/e 405 ($M^+$).

EXAMPLE 70

To a solution of o-fluoroaniline (3.9 g) in methylene chloride (50 ml), cooled to −20° under nitrogen, is added a solution of 2,4,4,6-tetrabromocyclohexadienone (35 mmol) in methylene chloride. After several hours, reaction is poured into 15% NaOH solution. The layers are separated and the organic fraction shaken against 15% NaOH solution. The methylene chloride fraction is washed with saturated NaCl solution, dried over calcium sulfate and evaporated to yield 4-bromo-2-fluoroaniline.

To the potassium salt of α-bromoisovaleric acid (1.42 g) is added 4-bromo-2-fluoroaniline (1.9 g). The mixture is heated at 125° under nitrogen for 3.5 hr and then cooled to RT. The reaction product is poured into 2 M NaOH and ether/chloroform. The basic phase is separated and acidified with conc. HCl and then extracted into ether, washed with saturated NaCl solution, dried over calcium sulfate and evaporated to yield N-(4-bromo-2-fluorophenyl)valine.

A mixture of N-(4-bromo-2-fluorophenyl)valine (0.45 g), potassium carbonate (0.25 g), THF (4 ml), DMF (4 ml) and m-phenoxy-α-cyanobenzyl mesylate (0.43 g) is stirred for about 60 hr and then poured into water and hexane/ether (9:1). The organic phase is washed with water and saturated sodium chloride solution, dried over calcium sulfate and evaporated. The residue is placed on prep. TLC eluting with 25% methylene chloride/hexane once and then 30% methylene chloride/hexane and the major band collected to yield the m-phenoxy-α-cyanobenzyl ester of N-(4-bromo-2-fluorophenyl)valine, MS m/e 496 (M+).

EXAMPLE 71

To 4.9 g of N-(4-chlorophenyl)valine (0.0215 mole) in 50 ml of 1,4-dioxane is slowly passed a stream of phosgene gas as the solution is stirred. Cooling is applied to keep the solution at RT. When the solution is saturated with phosgene, the phosgene is shut off and the mixture is allowed to stir under nitrogen at RT. After 45 hr, about two-thirds of the dioxane is removed by distilling at aspirator pressure. The residue is diluted with hexane, then allowed to crystallize overnight at RT. The solid is collected by filtration and washed with hexane, with care being taken to minimize exposure to air. The solid is dried in vacuo to yield 3-(4-chlorophenyl)-4-isopropyloxazolidine-2,5-dione, m.p. 137°–138°.

To a mixture of m-naphthoxybenzaldehyde (0.43 g), 3-(4-chlorophenyl)-4-isopropyloxazolidine-2,5-dione (0.5 g), and potassium cyanide (0.23 g) in benzene (about 10 ml), with stirring, is added benzyl triethyl ammonium chloride (about 0.1 g). The reaction mixture is stirred for about 50 hr. The reaction is then worked up by taking up in ether, washing with water and brine, drying over sodium sulfate and evaporating. The concentrate is plated, prep. TLC, eluting with 20% ether/hexane to yield the m-naphthoxy-α-cyanobenzyl ester of N-(4-chlorophenyl)valine, MS m/e 484 (M+).

NMR (CDCl₃) δ centered at 1.0 [m 6, (C$\underline{H}_3$)₂CH], 2.10 [m, 1, (CH₃)₂C$\underline{H}$], and

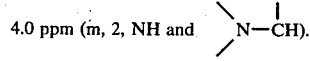

4.0 ppm (m, 2, NH and $\diagdown$N—CH).

EXAMPLE 72

The process of Example 69 is repeated using each of N-(2-chloro-4-trifluoromethylphenyl)valine, N-(4-chloro-2-fluorophenyl)valine, N-(2-fluoro-4-trifluoromethylphenyl)valine and N-(4-bromo-2-fluorophenyl)valine as the starting material to yield the m-phenoxybenzyl thiolester of
N-(2-chloro-4-trifluoromethylphenyl)valine,
N-(4-chloro-2-fluorophenyl)valine,
N-(2-fluoro-4-trifluoromethylphenyl)valine, and
N-(4-bromo-2-fluorophenyl)valine.

EXAMPLE 73

N-(2-fluorophenyl)valine, prepared by the reaction of 2-fluoroaniline and α-bromoisovaleric acid, is reacted with m-phenoxybenzyl bromide, as in Example 17, to yield the m-phenoxybenzyl ester of N-(2-fluorophenyl)valine, MS m/e 493.2 (M+).

Following the procedure of Example 28, there is prepared the hydrogen chloride salt of the m-phenoxybenzyl ester of N-(4-chlorophenyl)valine, m.p. 126°–130°.

EXAMPLE 74

Following the procedure of Example 6, 2-fluoro-4-chloroaniline is reacted with m-phenoxy-α-cyanobenzyl α-bromoisovalerate to give the m-phenoxy-α-cyanobenzyl ester of N-(2-fluoro-4-chlorophenyl)valine, MS m/e 452 (M+). Alternatively 2-fluoro-4-chloroaniline is reacted with the sodium salt of α-bromoisovaleric acid to give N-(2-fluoro-4-chlorophenyl)valine, which is then esterified using m-phenoxy-α-cyanobenzyl bromide or mesylate.

N-(4-chlorophenyl)valine is reacted with m-phenylcarbonylbenzyl bromide or the mesylate following the procedure of Example 24 to yield the m-phenylcarbonylbenzyl ester of N-(4-chlorophenyl)valine, MS m/e 421 (M+).

EXAMPLE 75

Each of N-(2-chloro-4-fluorophenyl)valine, N-(4-methylthiophenyl)valine, N-(4-chloro-3-fluorophenyl)valine, N-(4-cyano-2-fluorophenyl)valine, N-(4-bromo-2-fluorophenyl)valine and N-(4-trifluoromethoxyphenyl)valine is reacted with m-phenoxybenzyl bromide using the procedure of Example 24 to yield m-phenoxybenzyl ester of
N-(2-chloro-4-fluorophenyl)valine, MS m/e 427 (M+);
N-(4-methylthiophenyl)valine, MS m/e 421 (M+);
N-(4-chloro-3-fluorophenyl)valine, MS m/e 427 (M+, 200);
N-(4-cyano-2-fluorophenyl)valine, MS m/e 418 (M+);
N-(4-bromo-2-fluorophenyl)valine, MS m/e 471 (M+); and
N-(4-trifluoromethoxyphenyl)valine, MS m/e 459 (M+).

Following the procedure of Example 70, each of m-phenoxy-α-cyanobenzyl ester of N-(4-chloro-3-fluorophenyl)valine, MS m/e 452 (M+), and the m-phenoxy-α-cyanobenzyl ester of N-(2-fluoro-4-methylphenyl)valine, MS m/e 432 (M+), is prepared from N-(4-chloro-3-fluorophenyl)valine and N-(2-fluoro-4-methylphenyl)valine and m-phenoxy-α-cyanobenzyl mesylate or bromide. The starting materials are prepared by the reaction of 4-chloro-3-fluoroaniline and 2-fluoro-4-methylaniline, respectively, with the potassium salt of α-bromoisovaleric acid.

3-(Trifluoroacetyl)diphenyl ether (0.984 g) is dissolved in 5 ml methanol and reduced with 0.25 g sodium borohydride to give the corresponding alcohol. To 0.27 g of this alcohol (1.0 mole) is added 2 ml of pyridine and 0.5 g of 3-(4-chlorophenyl)-4-isopropyloxazolidine-2,5-dione (1.97 mole). The solution is heated at 80° for 15 hr under nitrogen. The reaction mixture is diluted with ether-hexane and washed with dilute hydrochloric acid followed by aqueous sodium bicarbonate. The organic phase is stripped and chromatographed on a 1 m silica plate eluted with 10% ether-hexane to give the 3-phenoxy-α-trifluoromethylbenzyl ester of N-(4-chlorophenyl)valine, MS m/e 477.1 (M+), 182 (100).

EXAMPLE 76

Following the procedure of Example 65, N-(4-chlorophenyl)valine is reacted with each of 5-benzyl-3-furylmethyl bromide, m-allyloxybenzyl bromide and m-propargyloxybenzyl bromide to yield the 5-benzyl-3-furylmethyl ester of N-(4-chlorophenyl)valine, MS m/e 397 (M+), the m-allyloxybenzyl ester of N-(4-chlorophenyl)valine, MS m/e 373 (M+), and the m-propargyloxybenzyl ester of N-(4-chlorophenyl)valine, MS m/e 371 (M+).

4-Chloroaniline is reacted with m-phenoxybenzyl 2-bromobutanoate using the process of Example 4 to yield m-phenoxybenzyl 2-(4-chlorophenylamino)butanoate, MS m/e 395 (M+).

Following the procedure of Example 6, 4-chloroaniline is reacted with each of p-benzylbenzyl α-bromoisovalerate and m-benzyl-α-cyanobenzyl α-bromoisovalerate to yield the p-benzylbenzyl ester of N-(4-chlorophenyl)valine, MS m/e 407 (M+), and the m-benzyl-α-cyanobenzyl ester of N-(4-chlorophenyl)valine, MS m/e 432 (M+).

Following the procedure of Example 60, N-(4-isopropoxycarbonylphenyl)valine is prepared and reacted with m-phenoxybenzyl bromide to yield the m-phenoxybenzyl ester of N-(4-isopropoxycarbonylphenyl)valine, MS m/e 461 (M+).

EXAMPLE 77

To a slurry of 0.50 g of sodium hydride in 25 ml of dioxane under argon is added 2.80 g of 2-(2-fluoro-4-trifluoromethylphenylamino)-3-methylbutanoic acid in small portions. When hydrogen evolution is ceased, the mixture is cooled in an ice bath and phosgene is passed over the surface of the stirring mixture. An obvious reaction ensues, with dissolution of the sodium salt and evolution of more hydrogen. When the hydrogen evolution appears to have ceased, the ice bath is removed and the addition of phosgene is continued until the solution appears nearly saturated. The reaction mixture is then filtered through a glass frit to remove insoluble salts and the filtrate is distilled at 15–20 mm pressure to remove phosgene and about 15 ml of the dioxane solvent. The residue is then diluted with hexane and allowed to stand at RT until crystallization is complete. The anhydride is collected by filtration, washed with hexane and dried under vacuum, with care being taken to minimize exposure to moisture, to yield 3-(2-fluoro-4-trifluoromethylphenyl)-4-isopropyloxazolidine-2,5-dione.

3-(2-Fluoro-4-trifluoromethylphenyl)-4-isopropyloxazolidine-2,5-dione is reacted with phenol using the procedure of Example 75 to give the phenyl ester of N-(2-fluoro-4-trifluoromethylphenyl)valine, which is reacted with NaHS using the method of Hirakayaski et al., *Bull. Chem. Soc. Japan* 38, 320 (1965) to give the sodium salt of the thioacid.

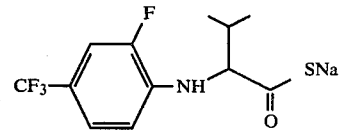

The thioacid is reacted with m-phenoxy-α-cyanobenzyl bromide or mesylate using the prcedure of Example 70 to yield the m-phenoxy-α-cyanobenzyl thiolester of N-(2-fluoro-4-trifluoromethylphenyl)valine.

EXAMPLE 78

Following the procedure of Example 38, N-(4-trifluoromethylphenyl)valine is reacted with p-benzoylbenzyl bromide to yield the p-benzoylbenzyl ester of N-(4-trifluoromethylphenyl)valine.

Each of 3-(2-fluoro-4-trifluoromethylphenyl)-4-isopropyloxazolidine-2,5-dione and 3-(4-trifluoromethylphenyl)-4-isopropyloxazolidine-2,5-dione, prepared by the procedure of Example 77, is reacted with m-benzoylbenzaldehyde and potassium cyanide using the procedure of Example 71 to yield the m-benzoyl α-cyanobenzyl ester of N-(2-fluoro-4-trifluoromethylphenyl)valin and the m-benzoyl-α-cyanobenzyl ester of N-(4-trifluoromethylphenyl)valine.

EXAMPLE 79

Each of N-(2-fluoro-4-trifluoromethylphenyl)valine, N-(2-chloro-4-trifluoromethylphenyl)valine, N-(4-chloro-2-fluorophenyl)valine and N-(4-bromo-2-fluorophenyl)valine is esterified using m-(o-fluorophenoxy)benzyl bromide according to the procedure of Example 42 to yield
the m-(o-fluorophenoxy)benzyl ester of
N-(2-fluoro-4-trifluoromethylphenyl)valine,
N-(2-chloro-4-trifluoromethylphenyl)valine,
N-(4-chloro-2-fluorophenyl)valine, and
N-(4-bromo-2-fluorophenyl)valine.

By repeating the above procedure using m-(p-fluorophenoxy)benzyl bromide as the esterification reagent, the respective m-(p-fluorophenoxy)benzyl ester of the listed amino acids are prepared.

EXAMPLE 80

Following the procedure of Example 38, N-(2-fluoro-4-methoxyphenyl)valine is prepared and reacted with each of m-phenoxybenzyl bromide and m-phenoxy-α-cyanobenzyl bromide to yield the m-phenoxybenzyl ester of N-(2-fluoro-4-methoxyphenyl)valine and the m-phenoxy-α-cyanobenzyl ester of N-(2-fluoro-4-methoxyphenyl)valine.

Using the process of Example 42, each of N-(2-fluoro-4-methoxyphenyl)valine and N-(2-fluoro-4-trifluoromethylphenyl)valine is reacted with m-(p-fluorophenoxy)benzyl bromide to yield the m-(p-fluorophenoxy)benzyl ester of N-(2-fluoro-4-methoxyphenyl)valine and the m-(p-fluorophenoxy)benzyl ester of N-(2-fluoro-4-trifluoromethylphenyl)valine.

EXAMPLE 81

Following the procedure of Example 17 or 42, N-(2-fluoro-4-trifluoromethylphenyl)valine is esterified using each of 2,6-dimethyl-4-allylbenzyl bromide, 2,6-dimethyl-4-propargylbenzyl bromide, 4-propargylbenzyl bromide, 4-phenyl-3-chloro-2-butene-1-yl bromide, 3,4-dichloro-α-ethynylbenzyl bromide, 3-trifluoromethoxybenzyl bromide, 3-trifluoromethyl-α-ethynylbenzyl bromide, 4-(p-fluorophenyl)-3-chloro-2-butene-1-yl chloride, 4-(o-fluorophenyl)-3-chloro-2-butene-1-yl chloride and 3-(2,2-dichlorovinyloxy)benzyl bromide to yield 2,6-dimethyl-4-allylbenzyl ester of N-(2-fluoro-4-trifluoromethylphenyl)valine, 2,6-dimethyl-4-propargylbenzyl ester of N-(2-fluoro-4-trifluoromethylphenyl)valine, 4-propargylbenzyl ester of N-(2-fluoro-4-trifluoromethylphenyl)valine 4-phenyl-3-chloro-2-butene-1-yl ester of N-(2-fluoro-4-trifluoromethylphenyl)valine, 3,4-dichloro-α-ethynylbenzyl ester of N-(2-fluoro-4-trifluoromethylphenyl)valine, 3-trifluoromethoxybenzyl ester of N-(2-fluoro-4-trifluoromethylphenyl)valine, 3-trifluoromethyl-α-ethynylbenzyl ester of N-(2-fluoro-4-trifluoromethylphenyl)valine, 4-(p-fluorophenyl)-3-chloro-2-butene-1-yl ester of N-(2-fluoro-4-trifluoromethylphenyl)valine, 4-(o-fluorophenyl)-3-chloro-2-butene-1-yl ester of N-(2-fluoro-4-trifluoromethylphenyl)valine, and 3-(2,2-dichlorovinyloxy)benzyl ester of N-(2-fluoro-4-trifluoromethylphenyl)valine.

Using the procedure of U.S. Pat. No. 3,979,519, the 3-trifluoromethoxy-α-cyanobenzyl ester of N-(2-fluoro-4-trifluoromethylphenyl)valine is prepared by the reaction of the acid chloride of N-(2-fluoro-4-trifluoromethylphenyl)valine and 3-trifluoromethoxybenzaldehyde cyanohydrin. Alternatively, 3-trifluoromethoxybenzaldehyde is reacted with 3-(2-fluoro-4-trifluoromethylphenyl)-4-isopropyloxazolidine-2,5-dione and potassium cyanide using the procedure of Example 71 herein to yield the 3-trifluoromethoxy-α-cyanobenzyl ester of N-(2-fluoro-4-trifluoromethylphenyl)valine.

Young lima bean leaves (in water) infested with approximately 50 adult *Tetranychus urticae* are sprayed to runoff with the compound (m-phenoxy-α-cyanobenzyl ester of N-phenylvaline) diluted to three different concentrations in aqueous carrier containing 0.025% Tween 20 and 0.1% wetting agent. The treated leaves are maintained at 24° and 16 hr photoperiod for 2 days. Live adult mites are then counted and substracted from the original total to obtain the number affected, which is stated as a percentage of the total. Correction is made for any control mortality using Abbott's formula. The compound had an LC$_{50}$ of less than 0.1%.

Individual fava bean leaves are dipped in the compound (the m-phenoxybenzyl ester of N-phenyl-N-methylvaline) diluted to three different concentrations in acetone with 0.025% Tween 20 and 0.1% wetting agent. The leaves are allowed to dry for 2 hr, then infested with 10 adult *Aphis fabae* caged on the upper surface of the leaves. The treated leaves are maintained for 48 hours at 24° and 16 hr photoperiod. The effect is stated as the number dead calculated as a percentage of the total aphids. This is corrected for control mortality, if any, using Abbott's formula. The compound had an LC$_{50}$ of less than 0.05%.

Fifteen 72-hr-old adult female *Musca domestica* L. are anesthetized with ether vapor. These are then treated with 1 ul of the compound [m-phenoxybenzyl ester of N-(p-methylphenyl)valine] diluted to three different concentrations in acetone applied to the dorsal surface of the prothorax. They are held in an assay container with milk-saturated cotton at 25°, 16 hr photoperiod for 24 hours. The effect is stated as the number dead calculated as a percentage of the total, corrected for any control mortality using Abbott's formula. The compound gave an LC$_{50}$ of less than 0.01%.

Into a mixture of 45 mg of wettable powder [Attaclay (60%), Marosperse N-22 (26.7%) of Igepon T-77 (13.3%)] and 0.5 ml of water containing the compound [m-phenoxybenzyl ester of N-(p-chlorophenyl)valine] at three different concentrations is dipped fifteen fed tick nymphs (Ornithodoros nymph I). The treated nymphs are maintained on filter paper for 7 days at 28°, 64% humidity, 16 hr photoperiod and then observed. Correction is made for any mortality in the control using Abbott's formula. The LC$_{50}$ of the compound was less than 0.01%.

Two groups of 10 each of 0–24 hr III instar *Heliothis virescens* larvae were treated with 1 ul of the compound [the m-phenoxybenzyl ester of N-(p-methoxyphenyl)valine] in acetone at three different concentrations by application to the dorsum of the thorax. Two groups of 10 each are treated identically with 1 ul acetone as controls. Larvae are held individually in 30 ml plastic cups provided with artificial medium for 72 hours at 25° and 16 hr photoperiod. After 72 hr the number of dead is calculated as a percentage of the total number originally treated and then corrected for any mortality in the control groups using Abbott's formula. The LC$_{50}$ of the compound was less than 0.5%.

Each of the compounds listed below were used to treat aphids (adult *Aphis fabae*) using the method described above. Each of the compounds gave an LC$_{50}$ of less than fifteen parts per million (ppm).

m-phenoxy-α-cyanobenzyl ester of N-(2-chloro-4-trifluoromethylphenyl)valine m-phenoxy-α-cyanobenzyl ester of N-(2-fluoro-4-trifluoromethylphenyl)valine m-phenoxybenzyl ester of N-(2-fluoro-4-trifluoromethylphenyl)valine m-phenoxybenzyl ester of N-(4-trifluoromethylphenyl)valine A 4E emulsive concentrate was prepared using the m-phenoxybenzyl ester of N-(4-trifluoromethyl)valine (51.3%), Atlox 3404F (3%), Atlox 3403F (3%) and Tenneco 500–100 (42.7%), was diluted with water and applied to *Tetranychus urticae* as described above. The LC$_{50}$ value was less than 10 ppm.

The compounds listed below were used to treat tick nymphs (Ornithodoros nymph I) using the method described above and exhibited an LC$_{50}$ of less than 15 ppm.

m-phenoxy-α-cyanobenzyl ester of N-(2-chloro-4-trifluoromethylphenyl)valine m-phenoxy-α-cyanobenzyl ester of N-(2-fluoro-4-trifluoromethylphenyl)valine m-phenoxy-α-methylbenzyl ester of N-(4-chlorophenyl)valine m-phenoxy-α-ethynylbenzyl ester of N-(4-chloro-2-fluorophenyl)valine m-phenoxy-α-ethynylbenzyl ester of N-(3-fluoro-4-methylphenyl)valine m-phenoxy-α-ethynylbenzyl ester of N-(2-fluoro-4-methylphenyl)valine m-phenoxy-α-cyanobenzyl ester of N-(2-fluoro-4-methylphenyl)valine m-phenoxy-α-cyanobenzyl ester of N-(4-chloro-2-fluorophenyl)valine Each of the compounds listed below was applied to *Heliothis virescens* larvae using the method described above and gave an LC$_{50}$ value of less than 0.1%.

m-phenoxybenzyl ester of N-(4-chloro-2-fluorophenyl)-valine m-phenoxy-α-cyanobenzyl ester of N-(4-chloro-2-fluorophenyl)valine m-phenoxybenzyl ester of N-(2-fluoro-4-trifluoromethylphenyl)valine m-phenoxy-α-cyanobenzyl ester of N-(4-bromo-2-fluorophenyl)valine m-phenoxybenzyl ester of N-(2-chloro-4-trifluoromethylphenyl)valine m-phenoxy-α-cyanobenzyl ester of N-(2-fluoro-4-trifluoromethylphenyl)valine m-phenoxy-α-cyanobenzyl ester of N-(2-chloro-4-trifluoromethylphenyl)valine m-phenoxybenzyl ester of N-(2-fluoro-4-methylphenyl)valine

What is claimed is:

1. A compound of the formula (A):

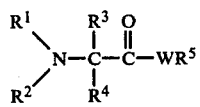

wherein,
W is oxygen or sulfur;
$R^1$ is the group

in which t is zero, one, two, three or four; Y is independently selected from hydrogen, lower alkyl, lower haloalkyl, lower alkoxy, lower alkylthio, lower alkylcarbonyl, lower alkoxycarbonyl, lower acyloxy, halogen, cyano, nitro, and lower haloalkylthio; and Z is independently selected from the values of Y, cycloalkyl, and lower haloalkoxy; or Y and Z form a methylenedioxy group;

$R^2$ is hydrogen, lower alkyl, lower haloalkylcarbonyl, or formyl;

$R^3$ is lower alkyl of 2 to 5 carbon atoms, lower alkenyl of 2 to 5 carbon atoms, lower haloalkyl of 1 to 4 carbon atoms, lower haloalkenyl of 2 to 4 carbon atoms, or lower cycloalkyl of 3 or 4 carbon atoms;

$R^4$ is hydrogen or fluoro; and $R^5$ is a group selected from:

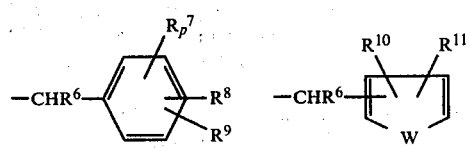

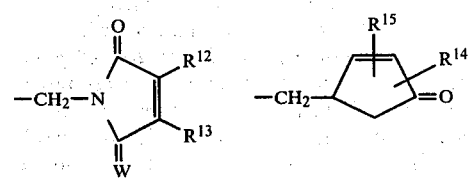

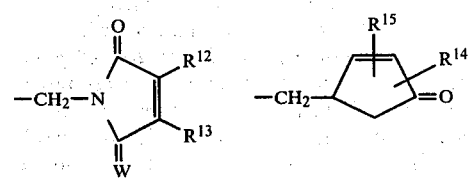

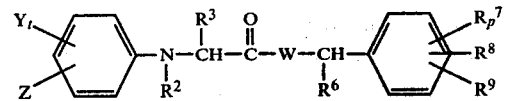

wherein,
p is zero, one, two or three;
$R^6$ is hydrogen, cyano, methyl, trifluoromethyl, ethynyl, or $$-\underset{NH_2}{C}=S;$$

$R^7$ is halogen, lower alkyl, lower haloalkyl, lower alkoxy, lower haloalkoxy, lower alkylthio, lower alkenyl, or lower haloalkenyl;

$R^8$ is hydrogen or together with $R^7$ forms a lower alkylenedioxy bridge across adjacent ring carbon atoms;

$R^9$ is hydrogen, lower alkenyloxy, lower alkynyl, lower alkynyloxy, lower haloalkynyl, lower alkylcarbonyl, arylcarbonyl, substituted arylcarbonyl, aryloxy, substituted aryloxy, arylthio, substituted arylthio, aralkyl, substituted aralkyl, cycloalkyl, cycloalkalkyl, lower acyloxy, aryloxycarbonyl, lower alkoxycarbonyl, or lower haloalkenyloxy;

$R^{10}$ is hydrogen or lower alkyl;

$R^{11}$ is hydrogen, lower alkenyl, lower alkynyl or aralkyl;

$R^{12}$ and $R^{13}$ taken together form a lower alkylene or a lower alkenylene bridge;

$R^{14}$ is hydrogen, lower alkyl, lower alkenyl, lower alkynyl, or aralkyl;

$R^{15}$ is hydrogen or lower alkyl;

$R^{16}$ is hydrogen, chloro, fluoro, or methyl;

$R^{17}$ is hydrogen, chloro, fluoro, methyl, or taken together with $R^{16}$ forms a carbon-carbon bond;

$R^{18}$ is phenyl or phenyloxy;

$R^{19}$ is hydrogen, halogen, methyl, or ethyl;

$R^{20}$ is allyl, propargyl, 3-butenyl, 3-butynyl, phenyl, or benzyl; and the salts thereof of strong inorganic acids or organic acids.

2. A compound according to claim 1 of the formula:

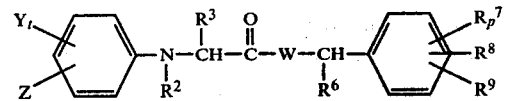

wherein $R^3$ is isopropyl, isopropenyl, or trifluoromethyl.

3. A compound according to claim 1 of the formula:

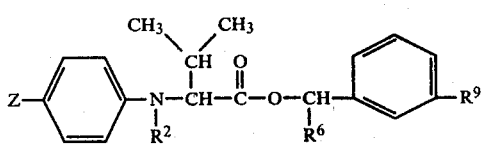

wherein,

Z is hydrogen, trifluoromethyl, fluoro, chloro, bromo, cyclopropyl or lower alkyl of 1 to 4 carbon atoms;

$R^2$ is hydrogen, methyl or ethyl;

$R^6$ is hydrogen, cyano, ethynyl or

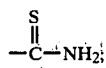

and $R^9$ is phenoxy or p-fluorophenoxy.

4. A compound according to claim 3 wherein each of $R^2$ and $R^6$ is hydrogen and $R^9$ is phenoxy.

5. A compound according to claim 1 of the formula:

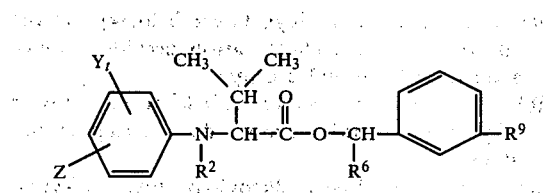

wherein, $R^2$ is hydrogen, methyl or ethyl;

$R^6$ is hydrogen, cyano, ethynyl or

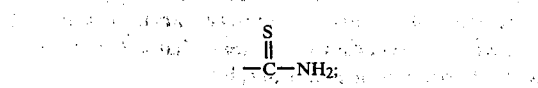

$R^9$ is phenoxy or p-fluorophenoxy;

Y is hydrogen, trifluoromethyl, fluoro, chloro, bromo, lower alkyl of 1 to 4 carbon atoms, lower alkoxy of 1 to 4 carbon atoms or lower alkylthio of 1 to 3 carbon atoms;

Z is independently selected from the values of Y, and cyclopropyl; and t is zero, one or two.

6. A compound according to claim 5 wherein t is one or two.

7. A compound according to claim 5 wherein t is zero.

8. A compound according to claim 5 wherein t is zero and Z is in the meta position.

9. A compound according to claim 5 wherein t is zero and Z is in the ortho position.

10. A compound according to claim 5 wherein t is one, Y is in the ortho position and Z is in the para position.

11. A compound according to claim 5 wherein t is one, Y is in the meta position and Z is in the para position.

12. A compound according to claim 11 wherein Y is fluoro.

13. A compound according to claim 10 wherein Y is fluoro.

14. A compound according to claim 6 wherein Z is lower alkyl of 1 to 4 carbon atoms, chloro, fluoro, bromo, trifluoromethyl or cyclopropyl; Z is in the para position; Y is in the ortho position; and t is one.

15. A compound according to claim 14 wherein Y is fluoro.

16. A compound according to claim 15 wherein each of $R^2$ and $R^6$ is hydrogen.

17. A compound according to claim 16 wherein $R^9$ is phenoxy.

18. A compound according to claim 15 wherein Z is lower alkyl of 1 to 4 carbon atoms.

19. A compound according to claim 18 wherein each of $R^2$ and $R^6$ is hydrogen.

20. A compound according to claim 19 wherein $R^9$ is phenoxy.

21. A compound according to claim 1 of the formula:

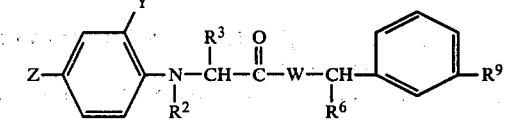

wherein $R^3$ is isopropyl, isopropenyl or trifluoromethyl.

22. A compound according to claim 21 wherein $R^2$ is hydrogen, $R^3$ is isopropyl, $R^6$ is hydrogen or cyano, $R^9$ is phenoxy, W is oxygen, and Y is bromo, chloro or fluoro.

23. A compound according to claim 1 of the formula:

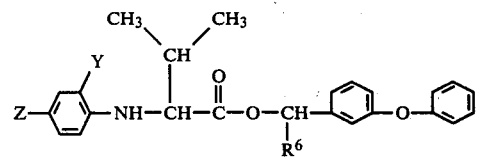

wherein $R^6$ is hydrogen or cyano.

24. A compound according to claim 23 wherein Y is fluoro and Z is chloro, bromo, fluoro, trifluoromethyl, or lower alkyl of one to four carbon atoms.

25. A compound according to claim 23 wherein Y is fluoro and Z is trifluoromethyl.

26. A compound according to claim 23 wherein Y is fluoro and Z is chloro.

27. A compound according to claim 23 wherein Y is chloro and Z is trifluoromethyl.

28. A salt according to claim 1 formed from a strong inorganic or organic acid.

29. A salt according to claim 28 formed from an acid selected from the group consisting of hydrochloric acid, sulfuric acid, phosphoric acid, p-toluenesulfonic acid, p-benzenesulfonic acid and methanesulfonic acid.

30. A salt according to claim 29 formed from hydrochloric acid.

31. A method for the control of pests such as insects and acarids which comprises treating said pests with a pesticidally effective amount of a compound according to claim 1, 26 or 27, or the salt thereof.

32. The method according to claim 31 wherein the pest is an insect of the order Lepidoptera, Orthoptera, Heteroptera, Homoptera, Diptera, Coleoptera, or Hymenoptera.

33. The method according to claim 31 wherein the pest is a mite or a tick of the order Acarina.

34. The method according to claim 33 wherein the mite is of the family Tetranychidae or Tarsonemidae.

35. A composition for the control of pests such as insects and acarids which comprises a suitable liquid or solid carrier and a pesticidally effective amount of compound according to claim 1, 26 or 27 or the salt thereof.

36. Isovaleric acid ester derivatives expressed by the general formula I:

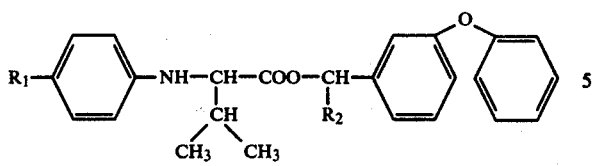

wherein,
- $R_1$ represents hydrogen, methyl group or chlorine atom, and
- $R_2$ represents hydrogen or cyano group.

37. Isovaleric acid ester derivatives according to claim 36, which are expressed by the general formula II:

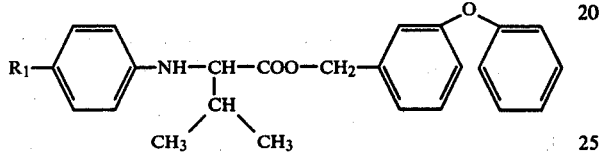

wherein $R_1$ represents the same meaning given in claim 36.

38. Isovaleric acid ester derivatives according to claim 36, which are expressed by the general formula III:

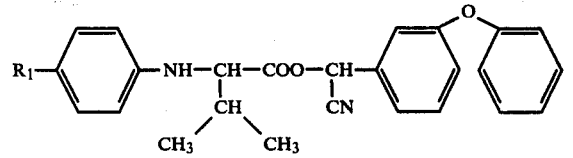

wherein $R_1$ represents the same meaning given in claim 36.

39. Compound according to claim 37, having the formula:

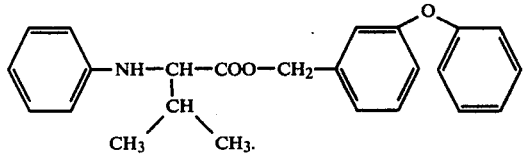

40. Compound according to claim 37 having the formula:

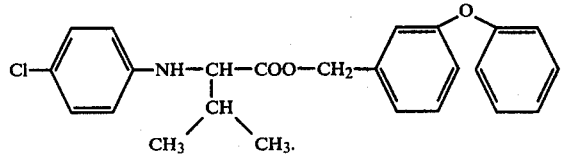

41. Compound according to claim 37 having the formula:

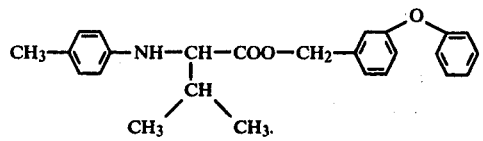

42. Compound according to claim 38 having the formula:

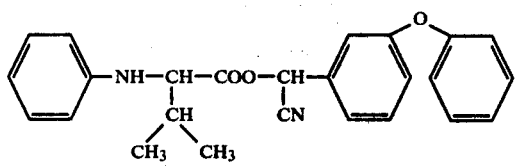

43. Compound according to claim 38 having the formula:

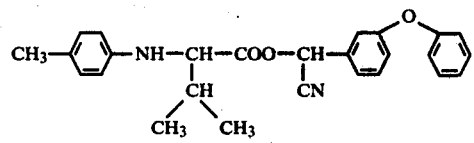

44. Compound according to claim 38 having the formula:

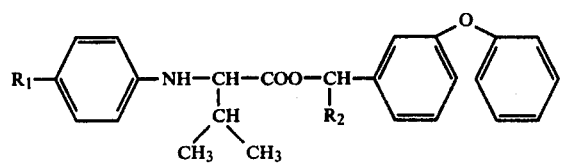

45. An insecticidal composition comprising a carrier and as its essential ingredient an insecticidally effective amount of an isovaleric acid ester derivative of the general formula:

wherein,
- $R_1$ represents hydrogen, a methyl group, or a chlorine atom and
- $R_2$ represents hydrogen or a cyano group.

46. An insecticidal composition according to claim 45 wherein $R_2$ is hydrogen.

47. An insecticidal composition according to claim 45 wherein $R_2$ is a cyano group.

48. An insecticidal composition according to claim 45 wherein $R_1$ is a chlorine atom and $R_2$ is hydrogen.

49. An insecticidal composition according to claim 45 wherein $R_1$ is a methyl group and $R_2$ is hydrogen.

50. An insecticidal composition according to claim 45 wherein $R_1$ is a chlorine atom and $R_2$ is a cyano group.

51. An insecticidal composition according to claim 45 wherein $R_1$ is a methyl group and $R_2$ is a cyano group.

52. The method of combatting insects which comprises treating the material to be protected with an insecticidally effective amount of an insecticidal composition as set forth in claim 45.

53. Process for producing isovaleric acid ester derivatives of the general formula:

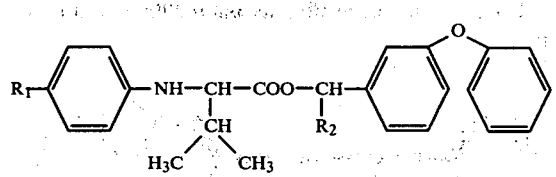

wherein:
R₁ represents hydrogen, methyl group or chlorine atom, and
R₂ represents hydrogen or cyano group which process is characterized by reacting a carboxylic acid or a reactive derivative thereof having the general formula:

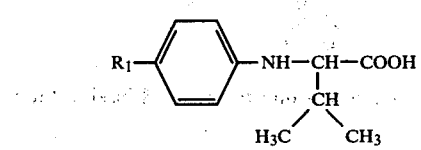

wherein,
R₁ represents the same meaning given above, with an alcohol or a reactive derivative thereof having the general formula:

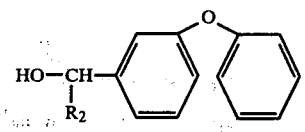

wherein
R₂ represents the same meaning given above.

54. The compound, m-phenoxy-α-cyanobenzyl ester of N-(2-chloro-4-trifluoromethylphenyl) valine, according to claim 23.

55. The compound, m-phenoxy-α-cyanobenzyl ester of N-(2-fluoro-4-trifluoromethylphenyl) valine, according to claim 23.

56. The compound, m-phenoxybenzyl ester of N-(4-trifluoromethylphenyl) valine, according to claim 3.

57. The compound, m-phenoxy-α-ethynylbenzyl ester of N-(2-fluoro-4-methylphenyl) valine, according to claim 5.

58. The compound, m-phenoxy-α-cyanobenzyl ester of N-(4-trifluoromethylphenyl) valine, according to claim 3.

59. The compound, m-phenoxybenzyl ester of N-(3-fluoro-4-methylphenyl) valine, according to claim 5.

60. The compound, m-phenoxybenzyl ester of N-(4-chloro-2-fluorophenyl) valine, according to claim 23.

61. The compound, m-phenoxybenzyl ester of N-(4-chloro-3-fluorophenyl) valine, according to claim 5.

62. The compound, m-phenoxy-α-cyanobenzyl ester of N-(2-fluoro-4-methylphenyl) valine, according to claim 23.

63. The compound, m-phenoxy-α-cyanobenzyl ester of N-(4-chloro-2-fluorophenyl) valine, according to claim 23.

* * * * *

UNITED STATES PATENT AND TRADEMARK OFFICE
CERTIFICATE OF CORRECTION

PATENT NO. : 4,411,912

DATED : October 25, 1983

INVENTOR(S) : Clive A. Henrick & Barbara A. Garcia

It is certified that error appears in the above—identified patent and that said Letters Patent is hereby corrected as shown below:

Col. 33, line 23, after "to" delete "a" second occurrence.

Col. 43, line 59, change "6" to --5--.

Signed and Sealed this

Twenty-fourth Day of April 1984

[SEAL]

Attest:

GERALD J. MOSSINGHOFF

Attesting Officer

Commissioner of Patents and Trademarks